(12) United States Patent
Liu et al.

(10) Patent No.: US 11,490,833 B2
(45) Date of Patent: Nov. 8, 2022

(54) APPARATUS AND METHOD FOR REMOTE RANGE-OF-MOTION TESTING

(71) Applicant: Medidata Solutions, Inc., New York, NY (US)

(72) Inventors: Jingshu Liu, Jersey City, NJ (US); Pramod Somashekar, Brooklyn, NY (US); Philip Beineke, Mountain View, CA (US); Andrew Howland, New York, NY (US); Francois Meunier, Atlantic Highlands, NJ (US); John Savage, Fair Haven, NJ (US)

(73) Assignee: MEDIDATA SOLUTIONS, INC., New York, NY (US)

( * ) Notice: Subject to any disclaimer, the term of this patent is extended or adjusted under 35 U.S.C. 154(b) by 988 days.

(21) Appl. No.: 15/641,075

(22) Filed: Jul. 3, 2017

(65) Prior Publication Data

US 2018/0256077 A1  Sep. 13, 2018

Related U.S. Application Data

(60) Provisional application No. 62/470,174, filed on Mar. 10, 2017.

(51) Int. Cl.
*A61B 5/11* (2006.01)
*A61B 5/00* (2006.01)
(Continued)

(52) U.S. Cl.
CPC .......... *A61B 5/1114* (2013.01); *A61B 5/0022* (2013.01); *A61B 5/1071* (2013.01);
(Continued)

(58) Field of Classification Search
CPC ... A61B 5/1114; A61B 5/1121; A61B 5/1071; A61B 2562/0219; A61B 5/459;
(Continued)

(56) References Cited

U.S. PATENT DOCUMENTS 7,602,301 B1 * 10/2009 Stirling ................ A61B 5/1124
340/573.1
8,954,289 B2   2/2015 Burton et al.
(Continued)

FOREIGN PATENT DOCUMENTS

WO   2008-067607 A1   6/2008
WO   2014/040023 A1   3/2014

OTHER PUBLICATIONS

The International Search Report and the Written Opinion of the International Searching Authority, PCT/2018/021763, dated Jun. 18, 2018.
(Continued)

*Primary Examiner* — Daniel L Cerioni
(74) *Attorney, Agent, or Firm* — Steptoe & Johnson LLP; Carl B. Wischhusen

(57) ABSTRACT

An apparatus for performing a remote test of range of motion of a person operating a user device includes a transceiver, a processor, and a display. The transceiver is configured to transmit a link to the user device and to receive motion data from the user device. The processor is configured to calculate in real time, based on the motion data, the position of the user device to enable real-time display to a test provider of the performance of the test and to determine in real time the quality of the test. The display is configured to show in real time a continuous indication of the performance of the test and quality results of the test. A method for performing a remote test of range of motion of a person operating a user device is also described and claimed.

20 Claims, 22 Drawing Sheets

(51) Int. Cl.
*A61B 5/107* (2006.01)
*G01C 5/06* (2006.01)
*G01C 17/04* (2006.01)
*G01P 15/08* (2006.01)
*G01P 15/14* (2013.01)

(52) U.S. Cl.
CPC .......... *A61B 5/1121* (2013.01); *A61B 5/7435* (2013.01); *A61B 5/459* (2013.01); *A61B 5/6898* (2013.01); *A61B 2562/0219* (2013.01); *G01C 5/06* (2013.01); *G01C 17/04* (2013.01); *G01P 15/08* (2013.01); *G01P 15/14* (2013.01); *G01P 2015/0865* (2013.01)

(58) Field of Classification Search
CPC ....... A61B 5/1117–1125; A61B 5/0022; A61B 5/7435
See application file for complete search history.

(56) References Cited

U.S. PATENT DOCUMENTS

| | | | |
|---|---|---|---|
| 2011/0201428 A1 | 8/2011 | Ferguson et al. | |
| 2012/0022884 A1* | 1/2012 | Chillemi | A61B 5/1121 705/2 |
| 2012/0075586 A1* | 3/2012 | Kirschen | A61B 3/028 351/239 |
| 2014/0163426 A1 | 6/2014 | Alberts et al. | |
| 2014/0257833 A1 | 9/2014 | Williams | |
| 2015/0133820 A1 | 5/2015 | Zohar et al. | |
| 2015/0142374 A1* | 5/2015 | Shibuya | A63B 69/3608 702/150 |
| 2015/0309563 A1* | 10/2015 | Connor | A61B 5/1124 340/573.1 |
| 2016/0270996 A1 | 9/2016 | Tong | |
| 2016/0338621 A1 | 11/2016 | Kanchan et al. | |
| 2017/0000386 A1* | 1/2017 | Salamatian | A61B 5/1122 |
| 2017/0007167 A1* | 1/2017 | Kostic | A61B 5/4064 |
| 2017/0132789 A1* | 5/2017 | Deitz | A61B 34/10 |
| 2019/0298253 A1* | 10/2019 | Hal | A61B 5/1128 |

OTHER PUBLICATIONS

Wang Lee et al., "A Smartphone-Centric System for the Range of Motion Assessment in Stroke Patients," IEEE Journal of Biomedical and Health Informatics, vol. 18(6), pp. 1839-1847 (Nov. 2014).

Seung Shin et al., "Within-day reliability of shoulder range of motion measurement with a smartphone," Manual Therapy, vol. 17(4), pp. 298-304 (Aug. 2012).

Giuseppe Matera et al., "The New Smartphone Application for Wrist Rehabilitation," The Journal of Hand Surgery (Asian-Pacific Volume), vol. 21(1), pp. 2-7 (Feb. 2016).

John Heukers, "A Smartphone-based Controller for Virtual Reality Applications," Bachelor's Thesis, University of Amsterdam (Jun. 27, 2014), retrieved from the Internet on Aug. 19, 2020: https://staff.fnwi.uva.nl/bredeweg/pdf/BSc/20132014/Heukers.pdf.

Extended European Search Report (supplementary European search report and European search opinion) dated Jul. 20, 2020, in EP Application No. 18764974.4.

Communication pursuant to Article 94(3) EPC for application No. EP 18764974.4, dated Mar. 12, 2021.

Communication pursuant to Article 94(3) EPC for Application No. 18764974.4, dated Aug. 6, 2021.

Ongvisatepaiboon, Kanmanus et al., "Smartphone-based Tele-Rehabilitation System for Frozen Shoulder Using a Machine Learning Approach," 2015 IEEE Symposium Series on Computational Intelligence, pp. 811-815.

Duffy, Jill, "10 Apps That Are Changing Healthcare," PC Magazine, Feb. 11, 2015.

Pourahmadi, Mohammad et al., "Reliability and concurrent validity of a new iPhone goniometric application for measuring active wrist range of motion: a cross-sectional study in asymptomatic subjects," 230 J. Anatomy 484-495 (2017).

Kim, T. et al., "A study on the measurement of wrist motion range using the iPhone 4 gyroscope application," 73(2) Ann. Plast. Surg. 215-18 (Aug. 2014) (Abstract only).

* cited by examiner

APPARATUS AND METHOD FOR REMOTE RANGE-OF-MOTION TESTING

CLAIM OF PRIORITY

This application claims priority from U.S. Provisional Application No. 62/470,174, filed on Mar. 10, 2017, which is incorporated by reference in its entirety.

BACKGROUND

A range-of-motion test is a test that is conducted on a patient's joint to measure the patient's ability to move the tested joint. A health care provider commonly performs range-of-motion testing following surgery to a patient's joint and during the post-operative therapy period to measure and track a patient's recovery. Additionally, it is common for a provider to perform range-of-motion testing on a patient's joint when that joint is affected by a disease, such as arthritis, to assess and monitor the disease's effect on the joint.

Traditionally, a provider performs range-of-motion testing in-person at the provider's facility, such as a hospital or clinic. The provider performs the range-of-motion test with a mechanical or digital instrument such as a goniometer or an inclinometer. Range-of-motion testing with instruments such as a goniometer or an inclinometer generally requires in-person testing because the provider must hold the instrument on or next to the patient's joint being measured.

BRIEF DESCRIPTION OF THE DRAWINGS

FIGS. 6-22 are depictions of the displays of the user device and provider device during a range-of-motion test process, according to embodiments of the present invention.

Figure 1:
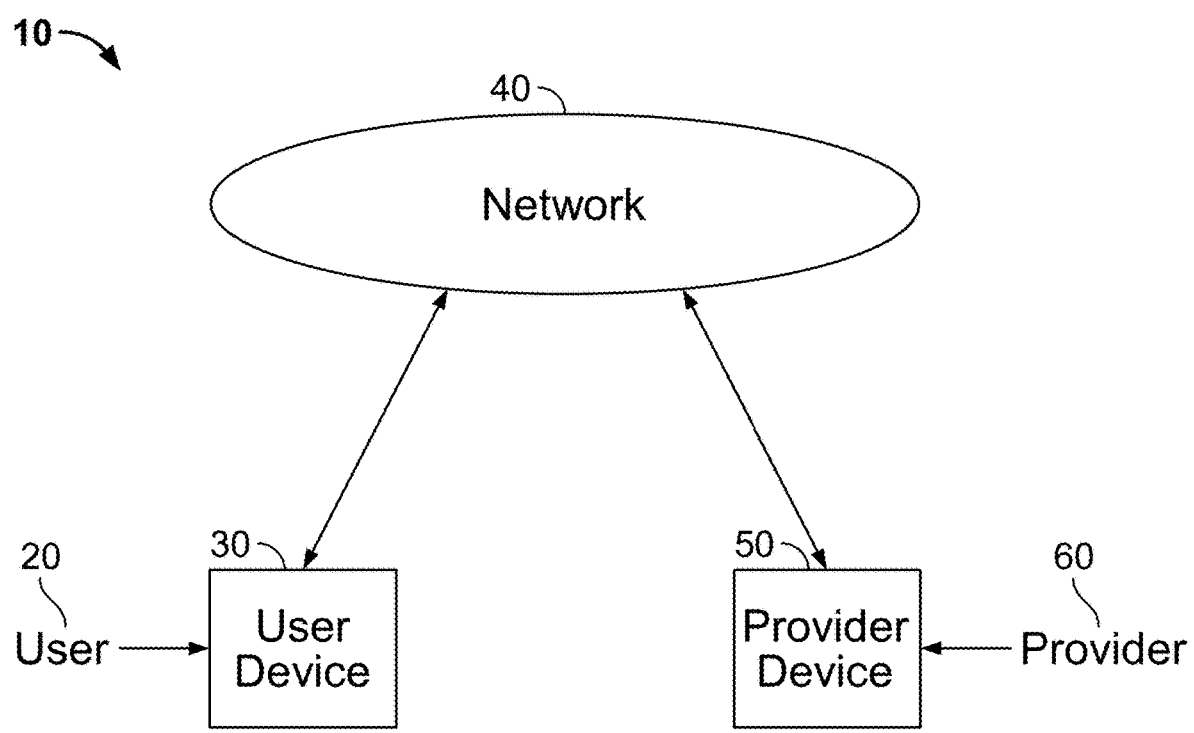
FIG. 1 is a system diagram generally illustrating the parties to and components of a remote range-of-motion test, according to an embodiment of the present invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of embodiments of the invention. However, it will be understood by those of ordinary skill in the art that the embodiments of the present invention may be practiced without these specific details. In other instances, well-known methods, procedures, components, and circuits have not been described in detail so as not to obscure the present invention.

Conventionally, a range-of-motion test may be administered by a health care provider, typically at the provider's facility, and requires the use of specialized equipment or tools. Conventional methods of administering range-of-motion tests require at least one party, typically the patient, to travel to the other party's location. Furthermore, the provider must subjectively determine if the test was executed properly and, therefore, whether the measured results are an accurate reflection of the patient's range of motion.

Given these problems, patients and providers responsible for administering range-of-motion testing on patients would benefit from a system that allows for remote testing, with the provider receiving substantially real-time feedback of the test's performance. Such benefits may include removing the burden of traveling to a health care provider's location to have a range-of-motion test administered in, which optimizes the patient's and health care provider's time, and having a computer system determine the test's satisfactory completion, which removes the health care provider's subjectivity from the testing process.

Reference is now made to FIG. 1, which shows a system diagram generally illustrating the parties to and components of a remote range-of-motion test, according to an embodiment of the present invention. System 10 includes user 20 who performs the range-of-motion testing remotely from provider 60. User 20 may be a patient or subject, who performs the range-of-motion testing via user device 30. User device 30 may be, for example, a cellular telephone or other mobile device that is operated by the user. User device 30 provides a communication platform for receiving and transmitting range-of-motion testing information from and to provider 60. Provider 60 in this example may be a healthcare provider, such as a doctor, nurse, or technician, or a test administrator who uses provider device 50 to interact with the subject performing the range-of-motion test remotely. Provider device 50 may be, for example, a computer, cellular telephone, or other type of computer or mobile device. Provider device 50 provides a communication platform for receiving and transmitting range-of-motion testing information from and to user 20.

In this example, user device 30 communicates with provider device 50 through network 40, which may be any network that allows for communications between electronic devices. Although network 40 is depicted as a singular network, the network may comprise more than one network. For example, network 40 may be any type of communications network, including a public or private telephone (e.g., cellular, public switched, etc.) network and/or a computer network, such as a WAN (wide area network), MAN (metropolitan area network), or LAN (local area network) or the Internet or an intranet. Communications to and from devices 30, 50 may be via transmission protocols that are well known to persons of ordinary skill in the art.

Figure 2A:
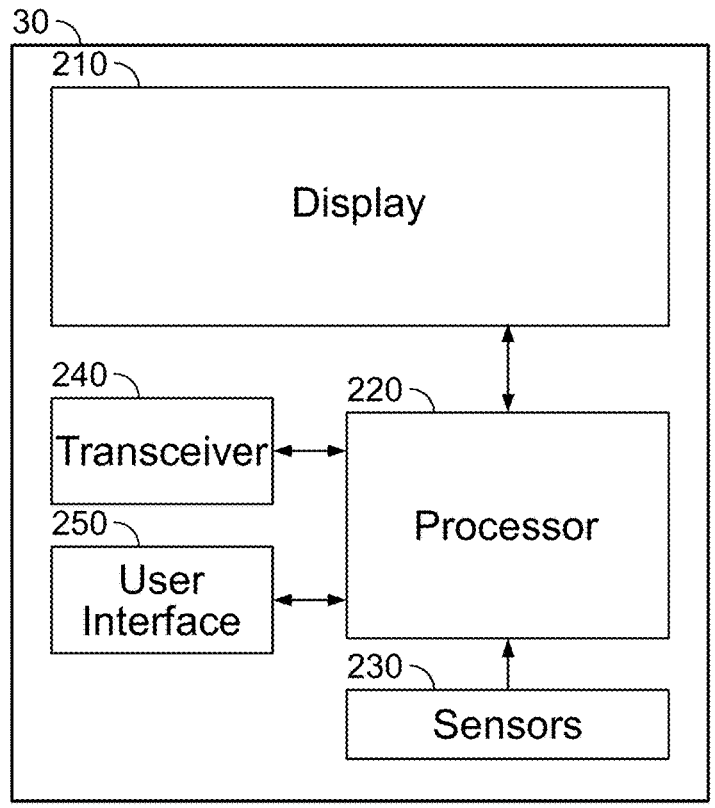
FIG. 2A is a block diagram of a user device, according to an embodiment of the present invention.

Reference is now made to FIG. 2A, which is a block diagram of user device 30, according to an embodiment of the present invention. User device 30 may include display 210, processor 220, sensors 230, transceiver 240, and user interface 250. Display (or monitor) 210 may display range-of-motion test information to user 20. User interface 250 may receive input from user 20. While user interface 250 is depicted as a component separate from display 210, display 210 and user interface 250 may be integrated to provide a screen that both displays information to user 20 and receives inputs from user 20. Sensors 230 may be micro electromechanical systems ("MEMS") inertial sensors. Types of MEMS sensors may include accelerometers to measure linear acceleration, gyroscopes to measure angular velocity, magnetometers to determine direction of earth's magnetic north, and pressure sensors to measure air pressure for altitude determinations. User's device 30 may include an accelerometer, gyroscope, and/or magnetometer to determine range of motion using the quaternion measure, as will be described below. Data from sensors 230 may be used to provide a continuous indication of performance of the range-of-motion test to user 20 and/or provider 60. Transceiver 240 may transmit and receive information through network 40. Transceiver 240 allows user device 30 to receive information (e.g., range-of-motion test instructions) from provider device 50 and send information (e.g., data from sensors 230) to provider device 50. Processor 220 may include program instructions for running user device 30's functionality.

Figure 2B:
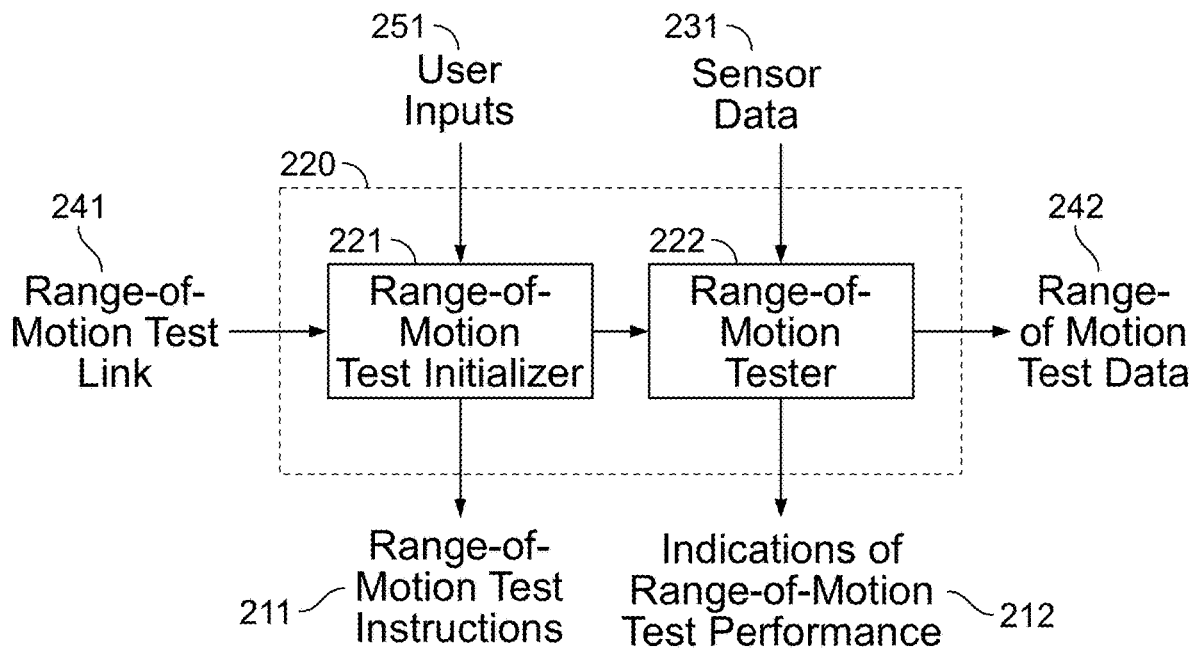
FIG. 2B is a more detailed block diagram of the processor of FIG. 2A, according to an embodiment of the present invention.

FIG. 2B is a more detailed block diagram of processor 220, according to an embodiment of the present invention. Processor 220 may include range-of-motion initializer 221 and range-of-motion tester 222. Processor 220 may include many other blocks or functionalities to control user device 30 that are not shown in FIG. 2B. Other blocks and functionalities of processor 220 are omitted to provide a clearer picture of an embodiment of the present invention.

Range-of-motion initializer 221 determines and sets up the range-of-motion test to be performed. By way of example, range-of-motion initializer 221 may receive instructions, including range-of-motion test link 241, from provider device 50. After the user receives and clicks on range-of-motion test link 241, range-of-motion initializer 221 begins setting up the range-of-motion test and, when indicated, commences the test. Range-of-motion test initializer 221 transmits range-of-motion test instructions 211 to user device 30's display 210. For example, range-of-motion initializer 221 may provide user 20 instructions on preparing for the test (e.g., how to hold user device 30 for the test), options for selecting certain types of range-of-motion tests (e.g., user 20 may choose an extension-flexion test, a pronation-supination test, or a radial-ulnar deviation test), and/or options for selecting the right/left hand of user 20. Range-of-motion initializer 221 determines that the range-of-motion test is set-up and then transmits an indication to user device 30's display 210 that the range-of-motion test should commence.

Range-of-motion tester 222 conducts the range-of-motion test. During the test, user device 30's sensors 230 continuously output sensor data 231 to range-of-motion tester 222. Range-of-motion tester 222 then transmits an indication 212 of performance of the test to user device 30's display 210. Additionally, range-of-motion tester 222 outputs range-of-motion test data 242 to provider device 50 through user device 30's transceiver 240. Range-of-motion test data 242 may include raw sensor data, processed data such as data indicating the test being performed, calculated range-of-motion test measurements, and/or data providing user device 30's calculated position in three-dimensional space.

Figure 3A:
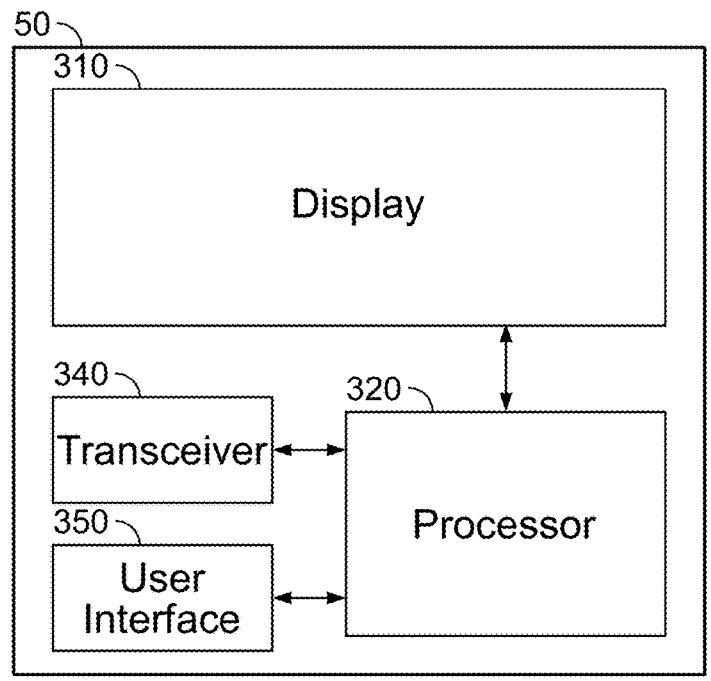
FIG. 3A is a block diagram of a provider device, according to an embodiment of the present invention.

Reference is now made to FIG. 3A, which is a block diagram of provider device 50, according to an embodiment of the present invention. Provider device 50 may include some of the same (or similar) items as user device 30, including display 310, processor 320, transceiver 340, and user interface 350. Display (or monitor) 310 may display range-of-motion test information to provider 60. User interface 350 may receive input from provider 60. Similar to user device 30, while user interface 350 is depicted as a component separate from display 310, display 310 and user interface 350 may be integrated to provide a screen that both displays information to provider 60 and receives inputs from provider 60. Transceiver 340 may transmit and receive information through network 40. Transceiver 340 allows provider device 50 to receive information (e.g., a substantially real-time, continuous stream of range-of-motion test performance information) and send information (e.g., a range-of-motion test link). Processor 320 may include program instructions for running provider device 50's functionality.

Figure 3B:
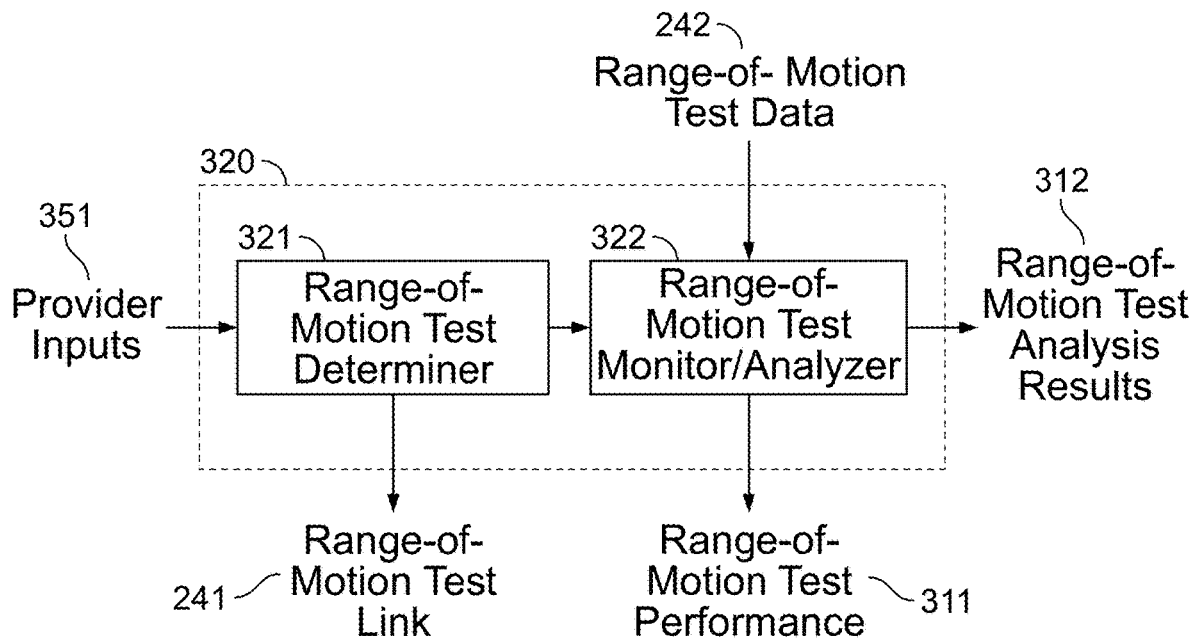
FIG. 3B is a more detailed block diagram of the processor of FIG. 3A, according to an embodiment of the present invention.

FIG. 3B is a more detailed block diagram of processor 320, according to an embodiment of the present invention. Processor 320 may include range-of-motion test determiner 321 and range-of-motion test monitor/analyzer 322. Processor 320 may include many other blocks or functionalities to control provider device 50 that are not shown in FIG. 3B. Other blocks and functionalities of processor 320 are omitted to provide a clearer picture of an embodiment of the present invention.

Range-of-motion test determiner 321 determines the range-of-motion test to be performed. By way of example, range-of-motion test determiner 321 may receive inputs 351 from provider 60. Based upon these inputs 351, range-of-motion test determiner 321 determines instructions, including range-of-motion test link 241, to transmit to user device 30.

Range-of-motion test monitor/analyzer 322 monitors the performance of the range-of-motion test and analyzes the range-of-motion test data to determine the quality of the test. Range-of-motion test monitor/analyzer 322 receives a substantially real-time and continuous stream of range-of-motion test data 242 and then transmits performance data 311 to provider device 50's display 310 in real-time for observation by provider 60. Performance data 311 may include the type of test being conducted, range-of-motion test data, and/or real-time three-dimensional images of user device 30 as it is being manipulated during the range-of-motion test. Despite user 20's remote location, provider 60 is shown a substantially real-time and continuous display of the device and testing data. Depending on the type of data being transmitted from user device 30 to provider device 50, range-of-motion test monitor/analyzer 322 may be responsible for processing user device 30's raw sensor data, data that indicate the test being performed, calculated range-of-motion test measurements, and/or user device 30's calculated three-dimensional position data.

Range-of-motion test monitor/analyzer 322 also analyzes range-of-motion test data 242 to determine the quality of the test, i.e., if it was satisfactory, which may be based on many factors. These factors may be programmed into range-of-motion test monitor/analyzer 322 such that range-of-motion test monitor/analyzer 322 produces a result for the range-of-motion test (e.g., "Good" or "Bad") without provider 60's intervention. Beneficially, provider 60's subjectivity in determining whether a test was satisfactory may be removed from the testing process. Other embodiments, however, may include accessing the judgment of provider 60.

Range-of-motion test monitor/analyzer 322 may use one or more of the following parameters to determine if a range-of-motion test was satisfactory: user device 30's starting position, the number of times user 20 completes the required movements, user device 30's movement orientation, and/or user device 30's range of movement. Regarding user device 30's starting position, the range-of-motion test instructions may require user 20 to start with user device 30 in a particular position for the test to be adjudged "Good." If this instruction is ignored, range-of-motion test monitor/analyzer 322 may output a result that the range-of-motion test was "Bad." For the number of times user 20 completes the required movements, the range-of-motion test instructions may direct user 20 to repeat a range-of-motion test multiple times to provide a more reliable measurement. If user 20 does not perform the minimum number of movements, range-of-motion test monitor/analyzer 322 may output a result that the range-of-motion test was "Bad." The frequency may be measured by half of the number of local optimum (i.e., maximum and minimum) of the measurement angle. An example of a lower bound to be set is 1.5.

With respect to user device 30's movement orientation, several sub-factors may be considered when determining whether user device 30's movement orientation is satisfactory: movement of the rotation axis, the correlation of angle measures, and the primary movement direction. More details regarding these sub-factors are provided below in discussing the measurement of the angles and axes. Regarding user device 30's range of movement, range-of-motion test monitor/analyzer 322 may output a determination that the range-of-motion test was "Bad" if user device 30's range of movement was beyond a threshold establishing the normal range, which would indicate that other joints that were not being tested were being moved simultaneously with the tested joint.

At the conclusion of range-of-motion test monitor/analyzer 322's analysis, range-of-motion test monitor/analyzer 322 will output results 312 (e.g., "Good" or "Bad"). Range-of-motion test analysis results 312 may be transmitted to provider device 50's display 310 and/or to provider device 50's transceiver 340 for transmission to user device 30. Range-of-motion test analysis results 312 may be transmitted prior to termination of the test if at any time during the test range-of-motion test monitor/analyzer 322 determines that the test is "Bad," e.g., user 20 did not start device 30 in the correct position. After completion of the range-of-motion test, user device 30's processor 220 may automatically proceed on to another range-of-motion test assigned by provider 60 or, if provider 60 assigned user 20 only one test, the program could terminate. Additionally, processor 320 may transmit range-of-motion test instructions to user device 30 that instruct user 20 to re-perform the range-of-motion test. Instructions to re-perform the range-of-motion test may be sent automatically from provider device 50 or may be sent after the health care provider inputs a request into provider device 50.

The blocks shown in FIGS. 2A, 2B, 3A, and 3B are examples of modules that may comprise system 10 and do not limit the blocks or modules that may be part of or connected to or associated with these modules. For example, there may be many more than just four parameters or factors that processor 320 uses to determine if a range-of-motion test was satisfactory. The range-of-motion test monitor/analyzer may be split into two or more blocks to more specifically address the monitoring and/or the analysis. Analysis of motion data and calculation of performance and results may be performed in user device 30, provider device 50, or a combination. The blocks in FIGS. 2A, 2B, 3A, and 3B may be implemented in software or hardware or a combination of the two, and may include memory for storing software instructions.

Figure 4:
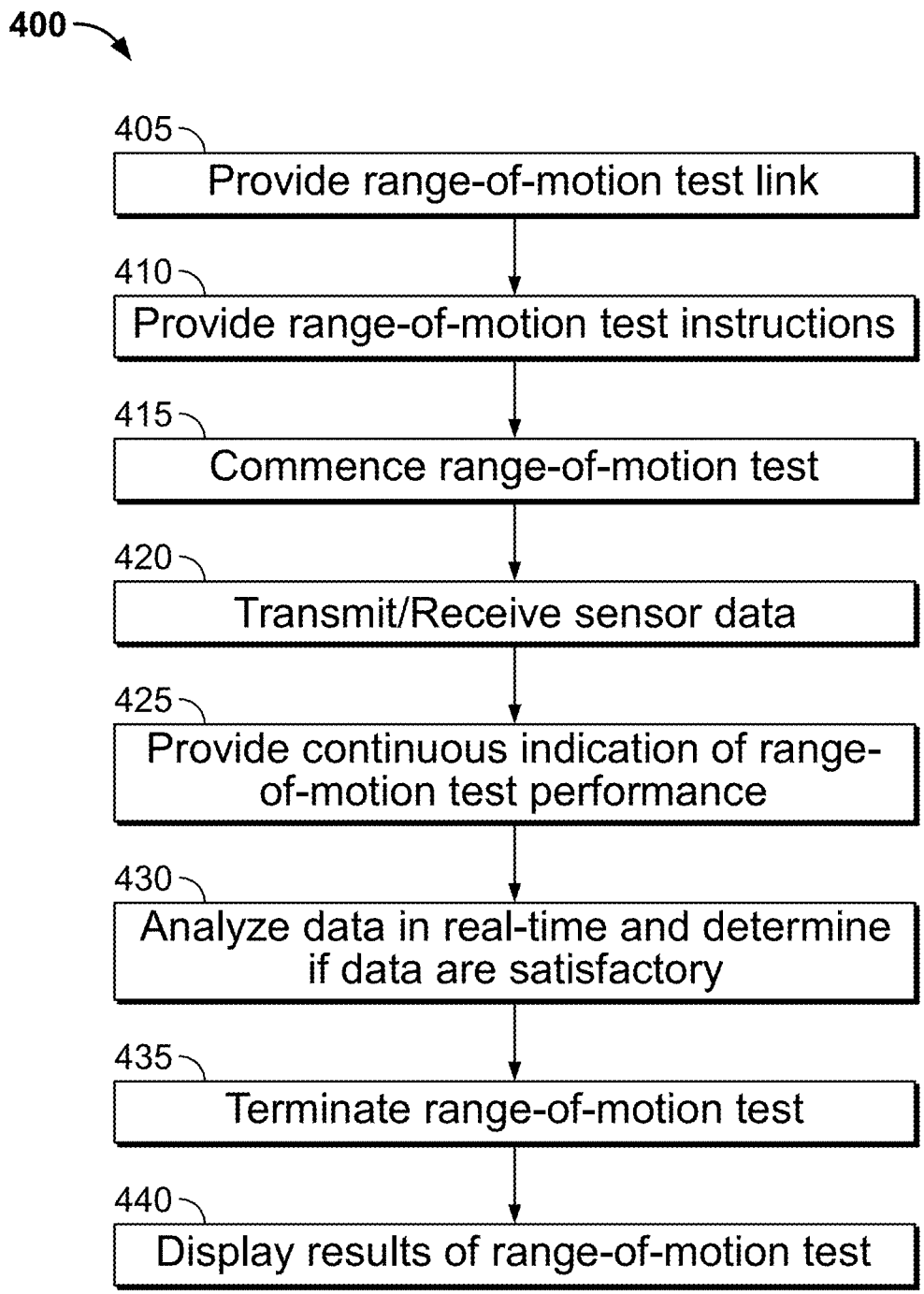
FIG. 4 is a flowchart illustrating how a remote range-of-motion test may be performed, according to an embodiment of the present invention.

Reference is now made to FIG. 4, which is a flowchart 400 illustrating how a remote range-of-motion test may be performed, according to an embodiment of the present invention. In operation 405, provider 60 determines the desired range-of-motion test for the particular user 20 and sends a link from provider device 50 to user device 30. User 20 then selects the link, which causes user device 30 to select/load the assigned range-of-motion test on user device 30.

In operation 410, user device 30 displays range-of-motion test instructions. By way of example, the range-of-motion test instructions may provide user 20 instructions on preparing for the test (e.g., how to hold user device 30 for the test), options for selecting certain types of range-of-motion tests (e.g., user 20 may choose an extension-flexion test, pronation-supination test, or a radial-ulnar deviation test), options for selecting the right/left hand of user 20, etc. After the range-of-motion test instructions have completed the set-up process for the range-of-motion test, user 20 may be prompted to commence the range-of-motion test, which is commenced in operation 415.

In operation 420, user 20 performs the assigned range-of-motion test with user device 30 such that user device 30's sensors 230 begin transmitting data indicating user device 30's movements during the range-of-motion testing. In operation 425, user device 30 provides a substantially real-time and continuous indication of the range-of-motion test performance to user device 30 and provider device 50. The substantially real-time and continuous indication of the range-of-motion test performance may include the type of test being conducted, the range-of-motion measured by user device 30, and/or a real-time three-dimensional image or depiction of the device as it is being manipulated during the range-of-motion test.

In operation 430, provider device 50 analyzes the substantially real-time range-of-motion test performance to determine if the range-of-motion test is being conducted satisfactorily. Alternatively, user device 30 may analyze the performance and transmit the analysis to provider device 50. As previously discussed, provider device 50 may use any or all of the following parameters to determine if the range-of-motion test was satisfactory: user device 30's starting position, the number of times user 20 completes the required movements, user device 30's movement orientation, and/or user device 30's range of movement.

In operation 435, the range-of-motion test is terminated. The range-of-motion test may be terminated by user 20, provider 60, automatically by user device 30, and/or automatically by provider device 50. In operation 440, the results of the range-of-motion test are displayed. As described above, the range-of-motion test results may be a simple "Good" or "Bad" indication or may be a more complex result that shows user 20 and/or provider 60 the precise indicators and/or attributes of the test that caused the test to be "Bad."

Besides the operations shown in FIG. 4, other operations or series of operations are contemplated to perform the remote range-of-motion test. Moreover, the actual order of the operations in the flowchart in FIG. 4 is not intended to be limiting, and the operations may be performed in any practical order.

Figure 5A:
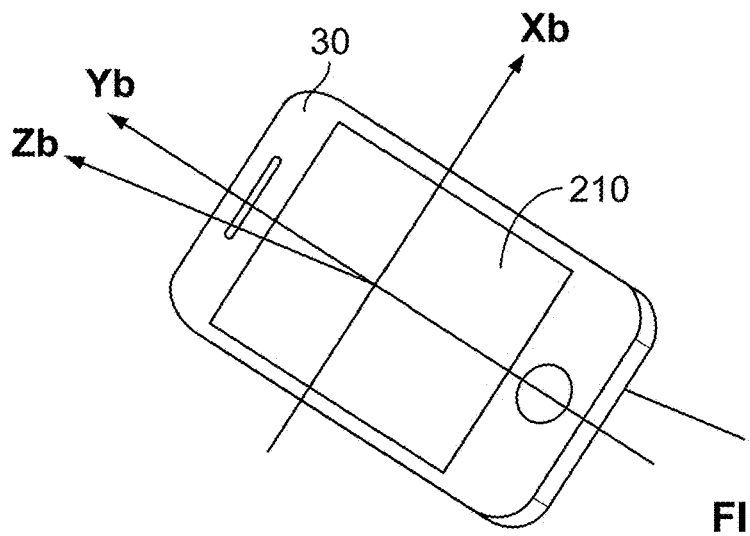
FIGS. 5A-5C show coordinate systems that may be used to determine the range-of-motion test performance, according to an embodiment of the present invention.
Figure 5B:
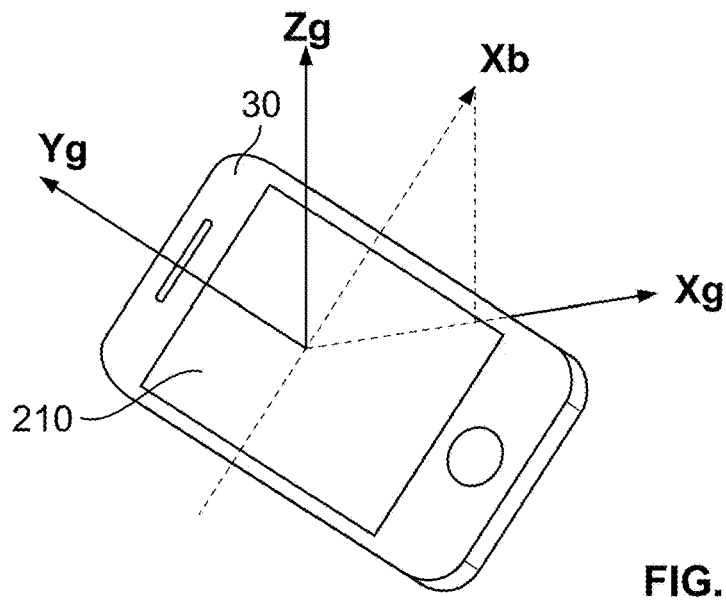
Figure 5C:
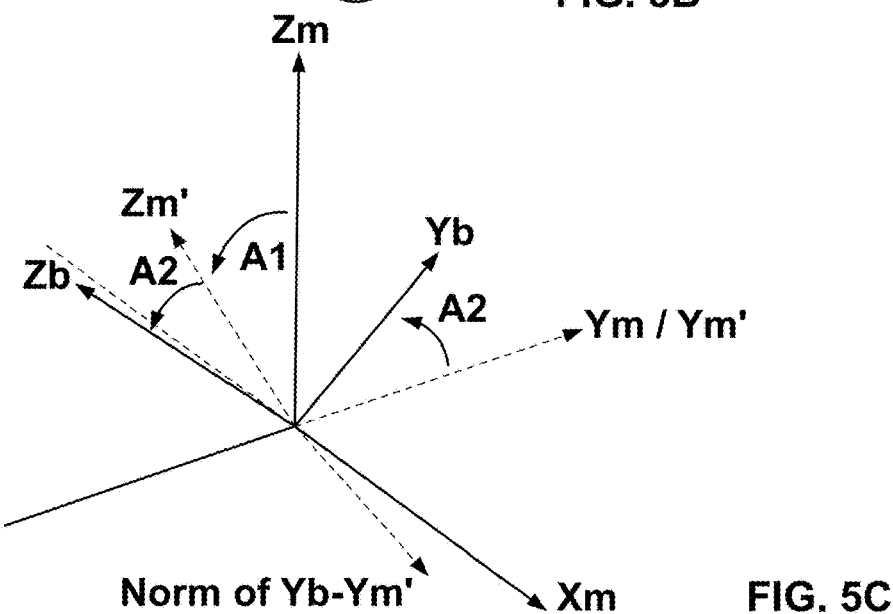

The determination of the quality of the range-of-motion test will now be discussed. Reference is now made to FIGS. 5A-5C, which show coordinate systems that may be used to determine the range-of-motion test performance, according to an embodiment of the present invention. FIGS. 5A and 5B respectively show two reference frames that are relevant to the orientation measure: the body frame and the global frame. The body frame is the coordinate frame fixed on the center of user device 30, denoted by $[x_b, y_b, z_b]$. As shown in FIG. 5A, $y_b$ is in the plane of user device 30's display 210 and is positive toward the top of display 210, $x_b$ is also in the plane of display 210 and is perpendicular to $y_b$ positive toward the right side of display 210, and $z_b$ is perpendicular to display 210 and is positive pointing away from display 210. The body frame is fixed relative to the device position, but is not fixed in space. The global reference frame may vary based on application and is denoted by $[x_g, y_g, z_g]$. As shown in FIG. 5B, by way of example, the global reference frame may be as follows: $z_g$ is perpendicular to the ground plane and is positive upward (away from the center of the earth), and $x_g$ and $y_g$ are determined as the projections of $x_b$ and $y_b$ to the ground plane at the starting position of user device 30. In this embodiment, $y_g$ overlaps $y_b$.

As discussed above, the range-of-motion test utilizes signals from user device 30's sensors 230, which may be MEMS sensors. While the range-of-motion test calculation may be performed in user device 30's processor 220 or provider device 50's processor 320, the following description assumes that the calculations are performed on user device 30 by processor 220. Processor 220 may produce the range-of-motion test values using sensors 230 and the quaternion, which is a four-element vector describing rotation in a three-dimension coordinate system. The quaternion may be described as follows:

$q=[w,x,y,z]^T=[\cos(\frac{1}{2}\theta), v_x \sin(\frac{1}{2}\theta), v_y \sin(\frac{1}{2}\theta), v_z \sin(\frac{1}{2}\theta)]$.

Intuitively, the quaternion may be thought of as describing a clockwise rotation of angle $\theta$ around a unit axis $v=[v_x, v_y, v_z]$ represented in the global reference frame.

The processor may also produce a rotation matrix that describes the body frame orientation relative to the global reference frame. The rotation matrix may be derived from the quaternion by:

$$R_g^b = [x_b(R), y_b(R), z_b(R)]$$
$$= \begin{bmatrix} w^2+x^2-y^2-z^2 & 2xy-2wz & 2xz+2wy \\ 2xy+2wz & w^2-x^2+y^2-z^2 & 2yz-2wx \\ 2xz-2wy & 2yz+2wx & w^2-x^2-y^2+z^2 \end{bmatrix}$$

The rotation matrix from one vector a to another vector b may be computed as follows. The axis u around which the rotation is made is the normalized cross product of a and b:

$$u_0 = a \times b$$
$$u = \frac{u_0}{\|u_0\|} = [u_x, u_y, u_z]$$

The angle $\theta$ of the rotation is the angle between a and b, which is given by:

$$\cos\theta = \frac{a^T b}{\|a\|\|b\|},$$

$$\sin\theta = \sqrt{1-\cos^2\theta}$$

Thus the matrix of a rotation by angle $\theta$ about the axis u in the direction of u is:

$$R = \begin{bmatrix} \cos\theta+u_x^2(1-\cos\theta) & u_x u_y(1-\cos\theta)-u_z\sin\theta & u_x u_z(1-\cos\theta)+u_y\sin\theta \\ u_x u_y(1-\cos\theta)+u_z\sin\theta & \cos\theta+u_y^2(1-\cos\theta) & u_y u_z(1-\cos\theta)-u_x\sin\theta \\ u_x u_z(1-\cos\theta)-u_y\sin\theta & u_y u_z(1-\cos\theta)+u_x\sin\theta & \cos\theta+u_z^2(1-\cos\theta) \end{bmatrix}$$

Reference is now made to FIG. 5C, which shows a movement reference frame that may be used to determine range-of-motion test performance for a wrist extension-flexion test, according to an embodiment of the present invention. The extension-flexion range-of-motion test describes extension, which is the movement of raising the back of the hand towards the wrist, and flexion, which is the movement of bending the palm towards the wrist. The following description of the extension-flexion range-of-motion test measurement assumes that (1) user 20 starts the test with palm flat facing the ceiling, and holding user device 30 with the top towards the thumb side and (2) user device 30 is parallel to the plane of user 20's palm at any time point. The movement reference frame in FIG. 5C has basis vectors $x_m$, $y_m$, $z_m$, that are used to decompose the wrist motion. Vector $x_m$ points to the arm direction and, based on the starting position assumption, is also parallel to the horizontal plane. Vector $y_m$ is perpendicular to $x_m$ and parallel to the horizontal plane, and vector $z_m$ is perpendicular to the horizontal plane. Given the assumption of the starting position, the movement reference frame is the same as the global reference frame, and therefore, in the following description both are referred to as the "movement reference frame."

High-frequency signals of the orientation of user device 30 are received throughout the test. Each signal may be regarded as a new ending orientation, and is compared with a common starting orientation where $[x_b, y_b, z_b]$ is the same as $[x_m, y_m, z_m]$, and arrive at a set of continuous angle measures. Given an ending orientation, the motion can be decomposed into first a rotation of angle $A_1$ around $y_m$, then some other types of rotation to arrive at the ending orientation. The angle $A_1$ is defined as the angle of extension-flexion, as the extension-flexion movement is a rotation around $y_m$. However, different rotation assumptions generally lead to different movement decomposition, resulting in slightly different rotation angles. The decomposition method used in this application is described as follows.

The following simplifying assumption of the wrist motion is made as shown in FIG. 5C: to get from orientation $[x_m, y_m, z_m]$ to orientation $[x_b, y_b, z_b]$ (body-frame x-axis is omitted in the figure), the subject first rotates around $y_m$ by angle $A_1$ to arrive at orientation $[x_{m'}, y_{m'}, z_{m'}]$ with $y_{m'}=y_m$; then rotates around the norm of plane $y_b$-$y_{m'}$ by an angle $A_2$ to arrive at $[x_b, y_b, z_b]$. The intuition is that a mechanical (i.e., an exact rotation around $y_m$) extension-flexion movement will have $y_b=y_m$, thus eliminating all the motion that resulted in an orientation change of $y_b$. The rotation matrix $R \in \mathbb{R}^{3\times 3}$ from $y_{m'}$ to $y_b$ may be calculated as described three paragraphs above. The angle measure may be obtained via:

$z_{m'}=z_b R^T, \cos A_1 = z_m^T z_{m'},$ assuming $z_m$, $z_{m'}$, and $z_b$ are unit vectors. Angle $A_1$ is further assigned to be positive if the projection of $z_{m'}$ onto $x_m$ is positive, and negative otherwise.

During testing, subjects may perform the desired movement multiple times. The angle $A_1$ is tracked throughout the test by the orientation of user device 30 at each sample time point to identify local minima and maxima. The range of movement is measured as the difference between successive local minima and maxima. Various summary statistics of the sequence of movements may be obtained; an embodiment of the present invention reports the median range of movement of each test.

Range-of-motion tests other than extension-flexion may be performed. In a radial-ulnar deviation test, radial deviation is the movement of bending the wrist to the thumb side, and ulnar deviation is the movement of bending the wrist towards the little finger side. The radial-ulnar deviation movement is a rotation around the $z_m$ axis rather than the $y_m$ axis. In a supination-pronation test, pronation describes the movement of rotating the palm towards the trunk of the body, and supination describes the movement of rotating the palm away from the trunk of the body. The supination-pronation movement is a rotation around the $x_m$ axis rather than the $y_m$ or $z_m$ axes. However, when evaluating the supination-pronation movement, the neutral position occurs when the hand is perpendicular to the ground plane with the palm facing the trunk of the body. Thus, 90° are added to the clockwise angle measure and subtracted from the counter-clockwise measure to determine the movement range.

Quality control (determination of a Good or Bad test) was discussed above and focused on four parameters: starting position, the number of times user 20 completes the required movements, user device 30's movement orientation, and user device 30's range of movement. Given the reference frames shown in FIGS. 5A-5C, the sub-factors of movement orientation—movement of the rotation axis, the correlation of angle measures, and the primary movement direction—are discussed in more detail. Device orientation may be monitored via the rotation matrix shown above, and the test may be determined to be "Bad" if the orientation deviates too much from the desired movement. To determine whether the rotation axis has moved too much, in extension-flexion movement, $y_b$ should overlap $y_m$ and the movement is a rotation around $y_b$. In the ideal case, the $z_m$-$y_b$ angle (the angle between vectors $z_m$ and $y_b$) would be constantly around 90°. This angle is measured during the test, and the subject is notified if the range of angle change is larger than a certain threshold. This controls for the scenario in which the test is extension-flexion while the subject primarily performed supination-pronation. A similar approach applies to the other two types of tests: for supination-pronation, the $z_m$-$x_b$ angle is monitored, and for radial-ulnar deviation, the $z_m$-$z_b$ angle is monitored.

Regarding correlation of angle measures, because the desired movement is a rotation around one of the body frame axes, the movement of the other two body frame axes should be highly correlated. Using extension-flexion movement as an example, $z_b$ and $x_b$ should move together. Thus, the correlation between the $z_m$-$z_b$ angle and the $z_m$-$x_b$ angle is monitored, and the subject is notified if the correlation drops below a certain threshold. This criterion identifies cases in which the test is extension-flexion while the subject primarily performed radial-ulnar deviation. A similar approach applies to the other two types of tests.

The primary movement direction is measured to determine how much it deviates from the desired direction. In the extension-flexion test, the primary movement direction is defined as follows: project the trace of the top of $z_b$ onto the $x_m$-$y_m$ plane, and the primary component direction, which may be measured by the regression coefficient because the projections are in a two-dimensional space, is the primary movement direction. In an ideal extension-flexion test, the primary direction will align well with the $x_m$ direction. The angle between the primary movement direction and the $x_m$ vector is then measured, and the test is determined to be "Bad" if the angle is larger than a certain threshold. An extreme example that will pass the other two orientation criteria but not this one occurs as follows: the subject turns the device in his or her palm after the test begins, so that the top of the device is aligned with the subject's four fingers, then the subject performs a supination-pronation test instead of the extension-flexion test. Similar measurements are derived for the other two tests: in the supination-pronation test, $z_b$ is also projected onto the $x_m$-$y_m$ plane, and the primary movement direction should align with $y_m$. In the radial-ulnar deviation test, $x_b$ is projected onto the $y_m$-$z_m$ plane, and the primary movement direction should align with $y_m$.

Reference is now made to FIGS. 6-22, which are depictions of the displays of both user device 30 (left or "subject" side) and provider device 50 (right or "provider" side) during a range-of-motion test process, according to embodiments of the present invention. The particular joint being tested in these embodiments of the present invention is the wrist. User device 30 in these embodiments is a smartphone with a touch screen, and provider device 50 is a computer, but the invention is not limited to these specific devices.

Figure 6:
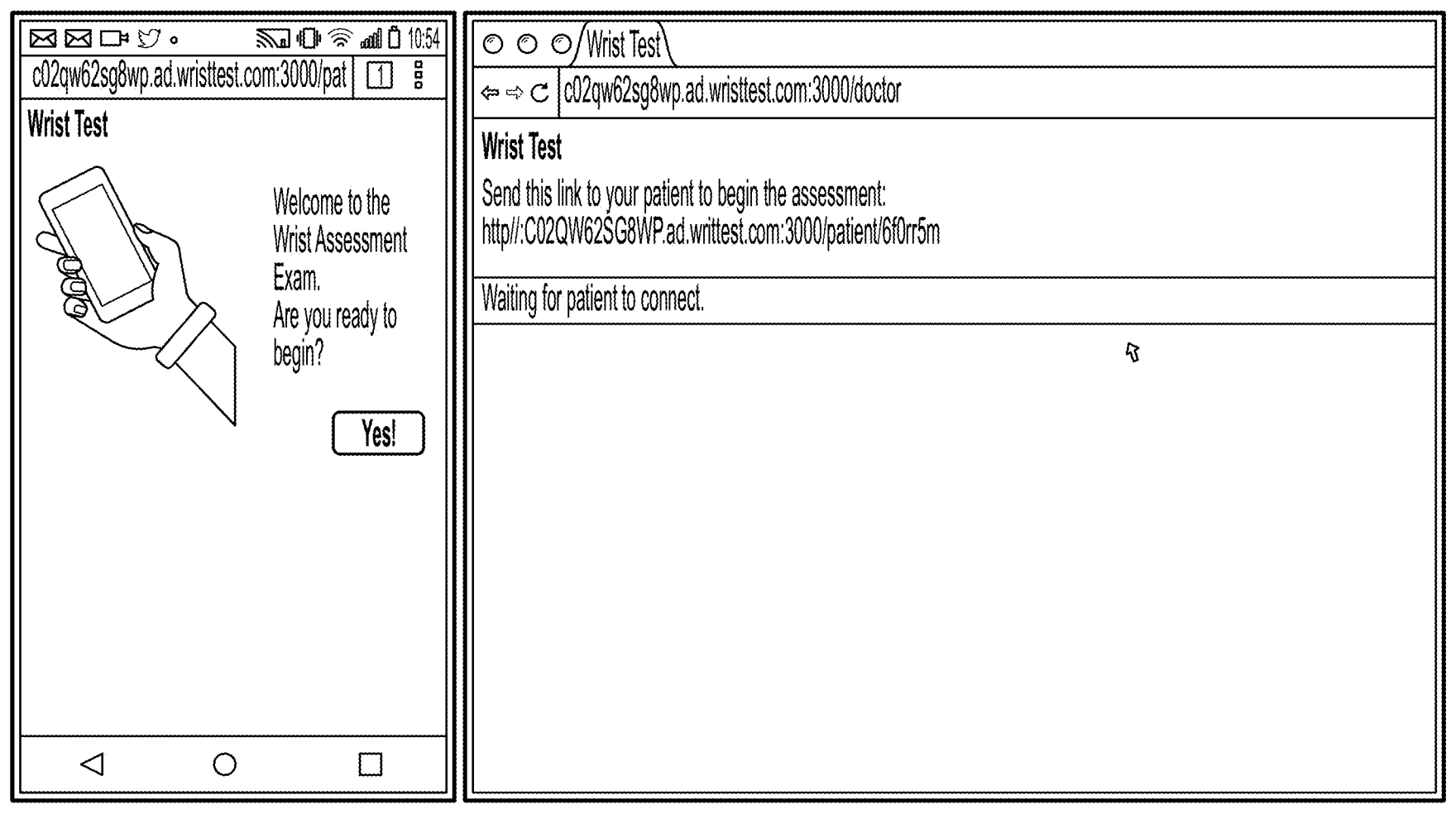
Figure 7:
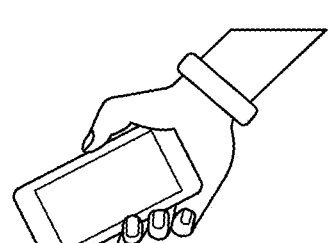
Figure 8:
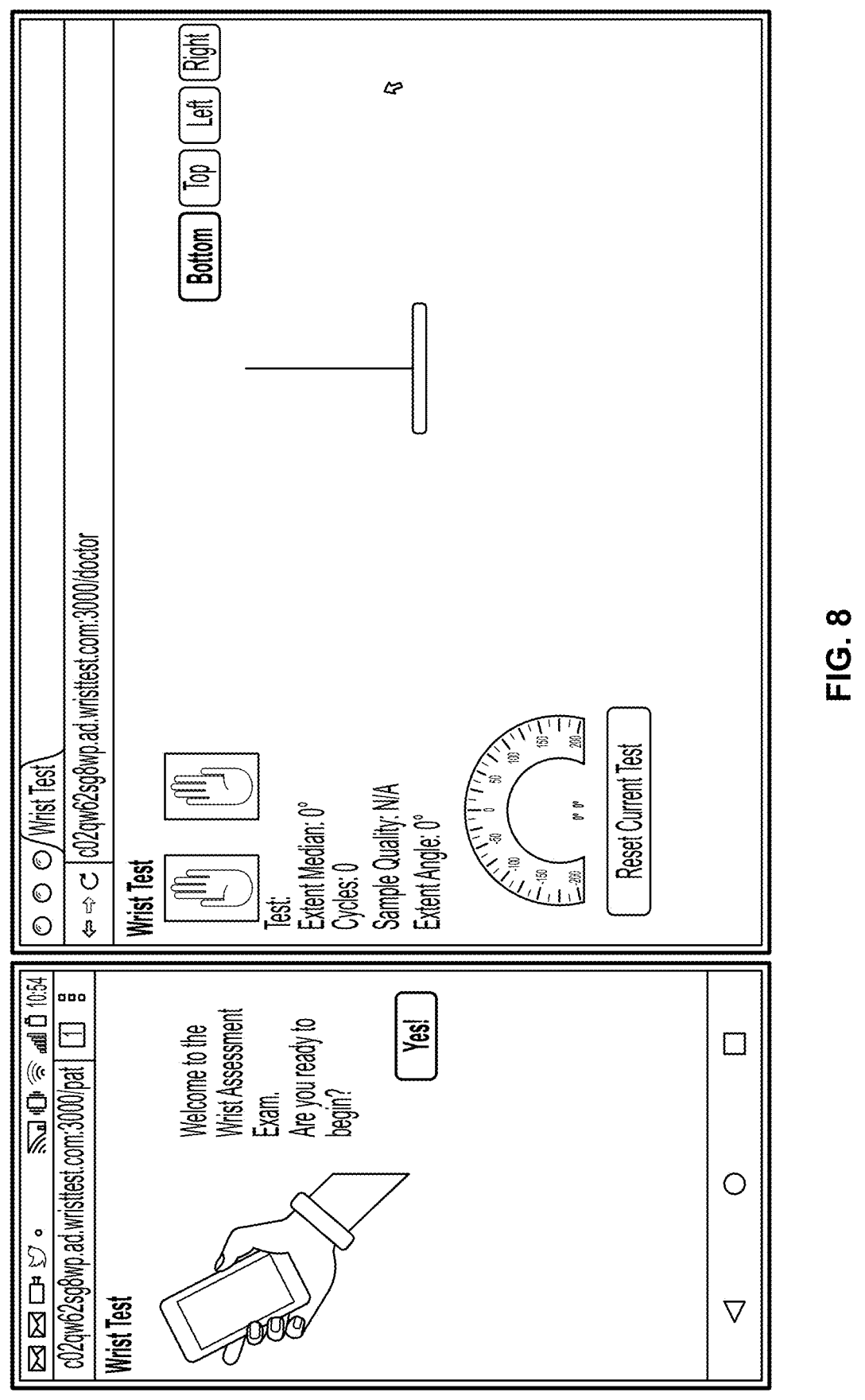
Figure 9:
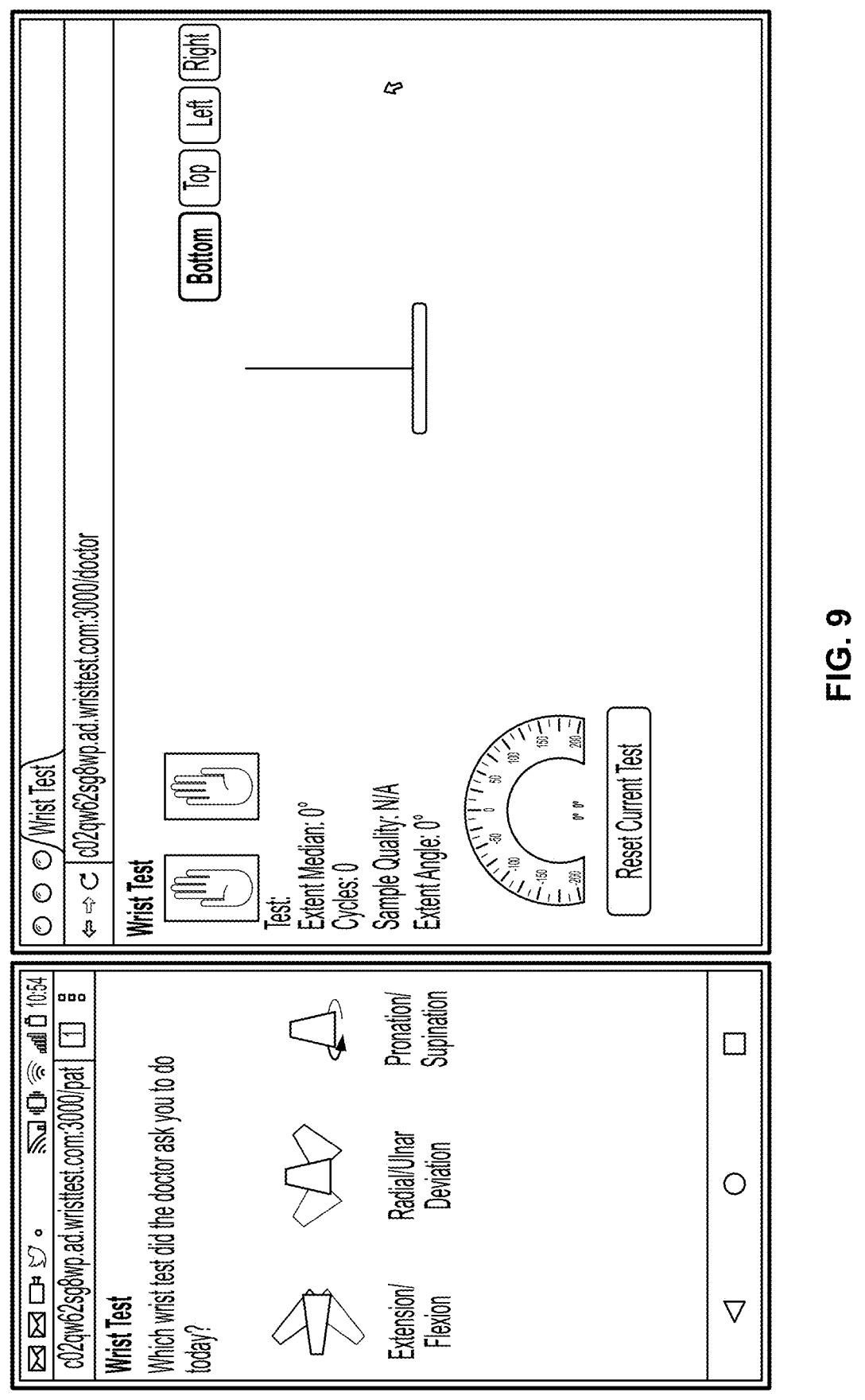
Figure 10:
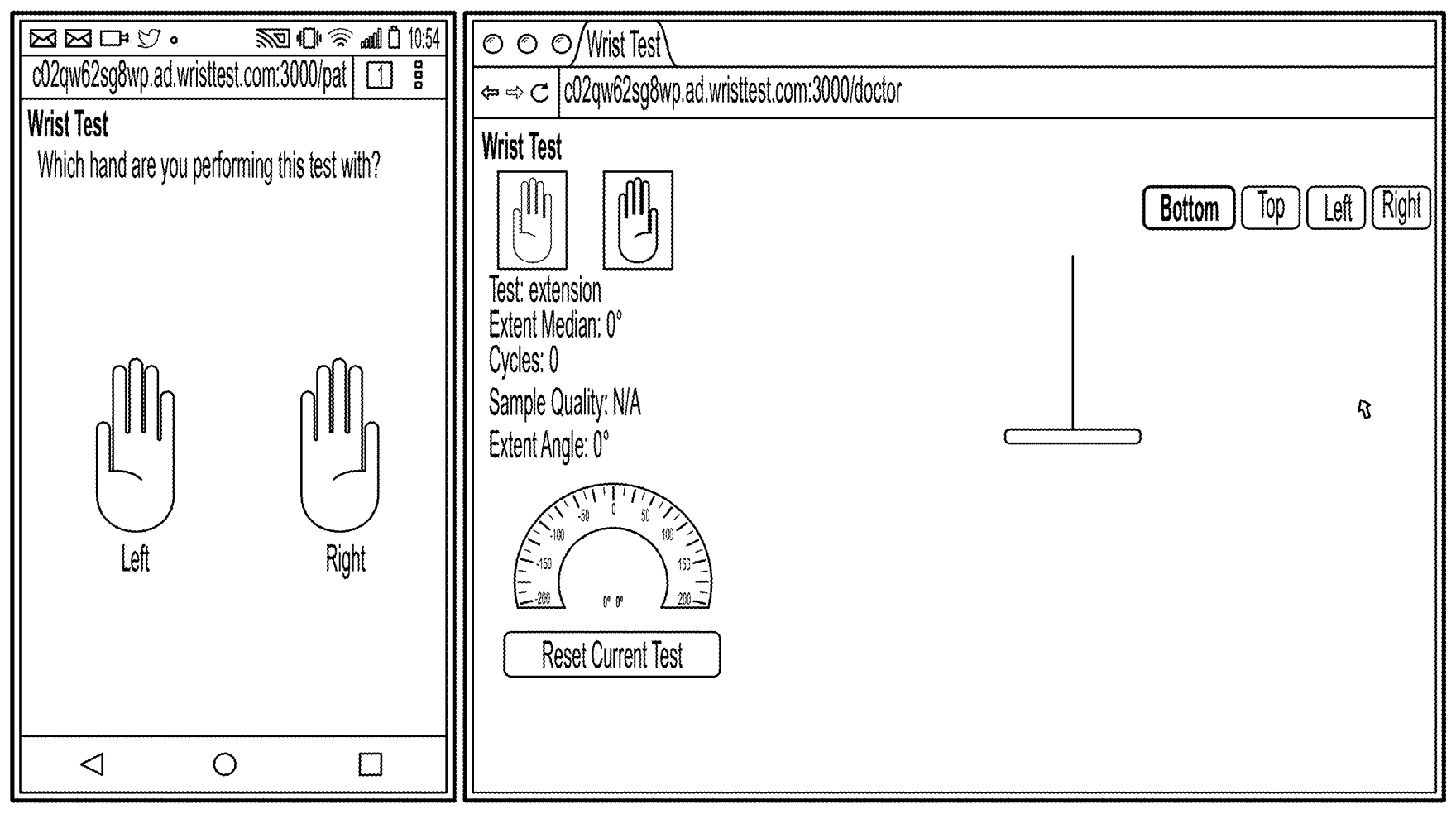
Figure 11:
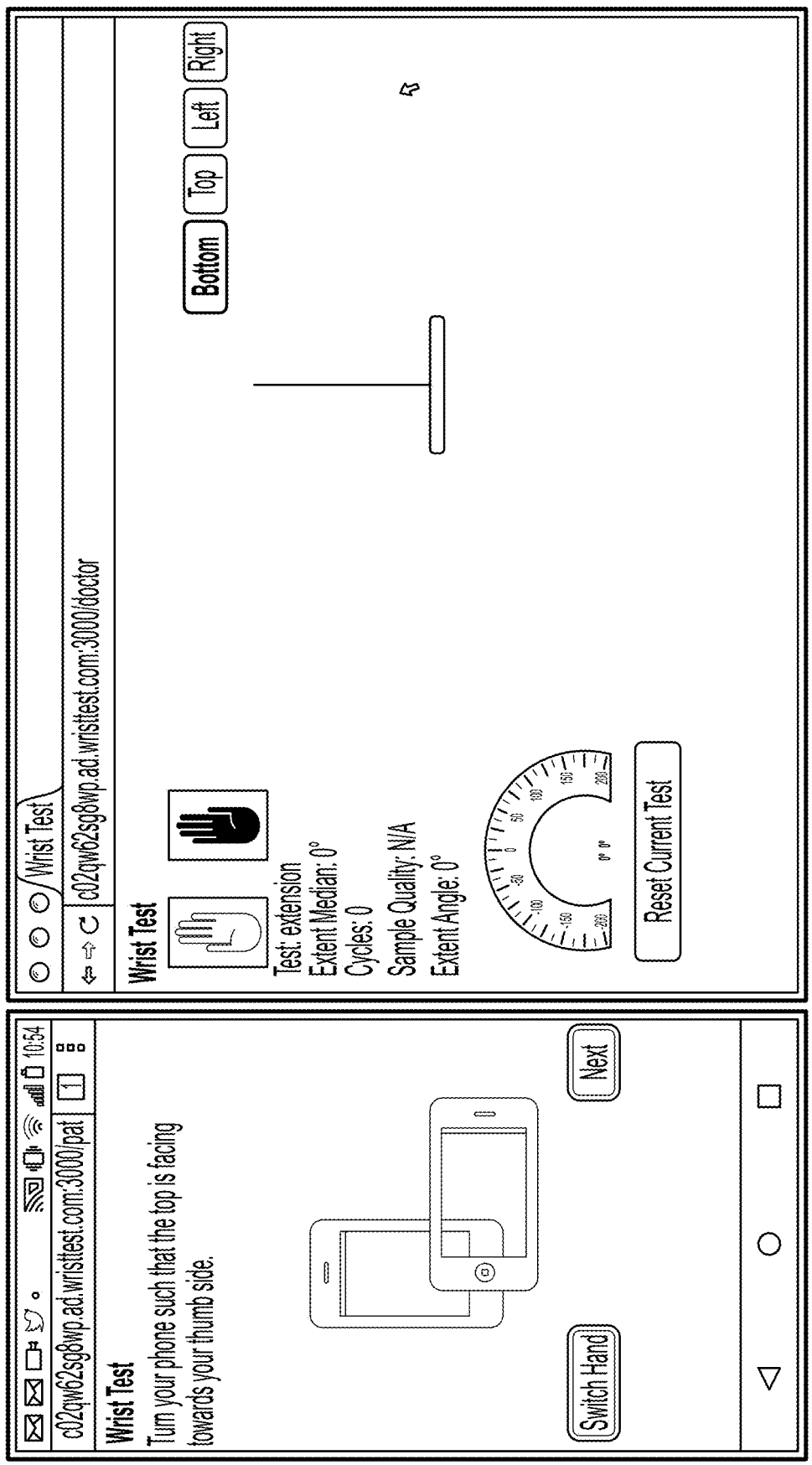

In FIG. 6, the provider sends the subject a link to begin the test. The subject clicks on the "YES!" button to begin. In FIG. 7, the provider is notified that the subject clicked on the link and is connected and ready to begin the test. The provider clicks on the "Next" button to start the test. In FIG. 8, the provider's display changes to show the test screen, along with a red "Reset Current Test" button so that the provider may reset the test and have it performed again, if desired. In FIG. 9, the display asks the subject to select the particular wrist test that the provider directed the subject to perform. The choices in this embodiment are extension-flexion, radial-ulnar deviation, and pronation-supination. The subject chooses "extension-flexion," as shown on the provider side of FIG. 10 ("Test" now says "extension"). In FIG. 10, the display asks the subject which hand will be tested. The subject chooses the right hand, as shown on the provider side of FIG. 11 (the right hand turns black). In FIG. 11, the display directs the subject to establish the initial device position for the particular range-of-motion test. FIG. 11 also shows that the subject display provides the subject with a clickable "Next" link, which will send the subject to the testing screen, and a clickable "Switch Hand" link, which allows the subject to switch hands.

Figure 12:
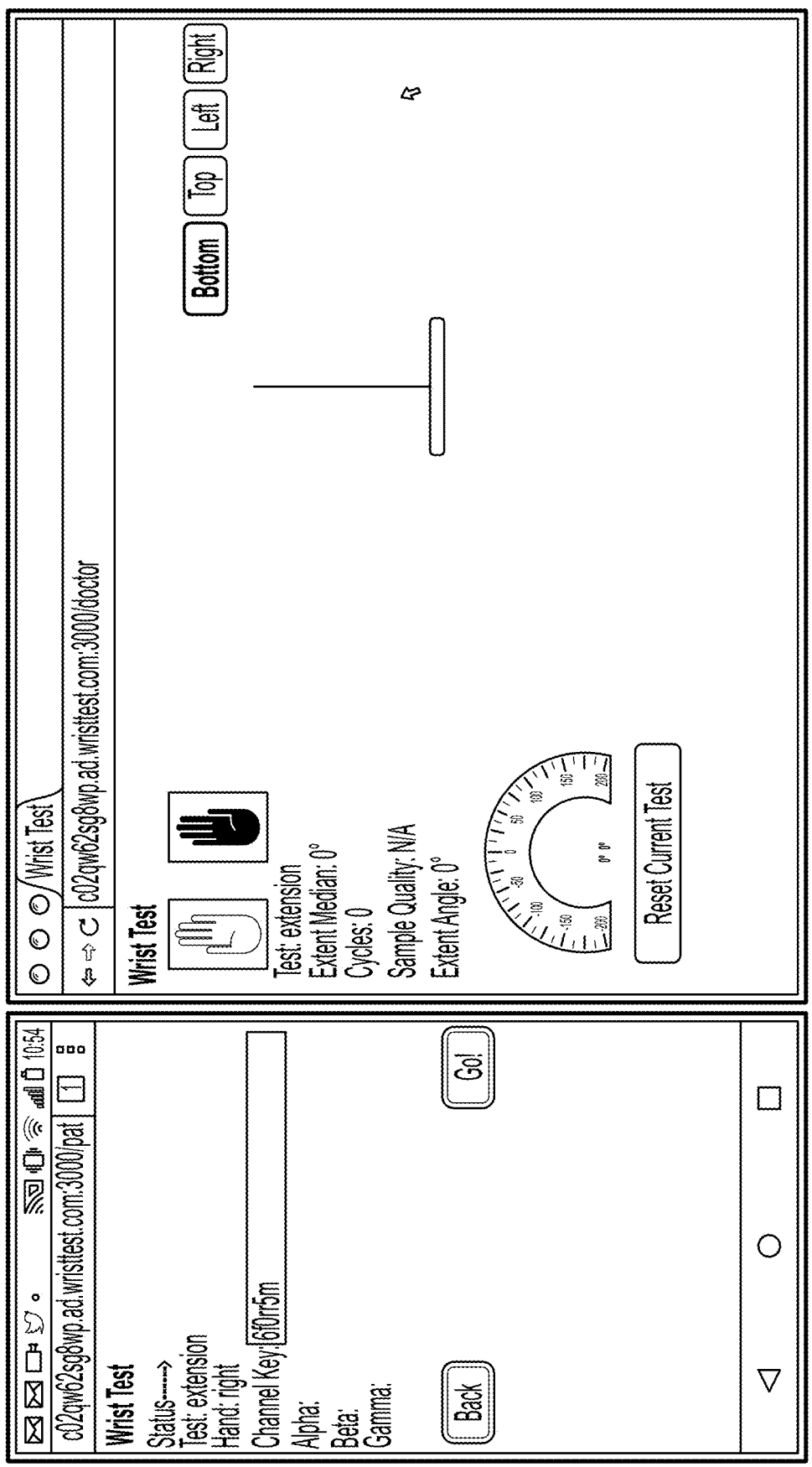
Figure 13:
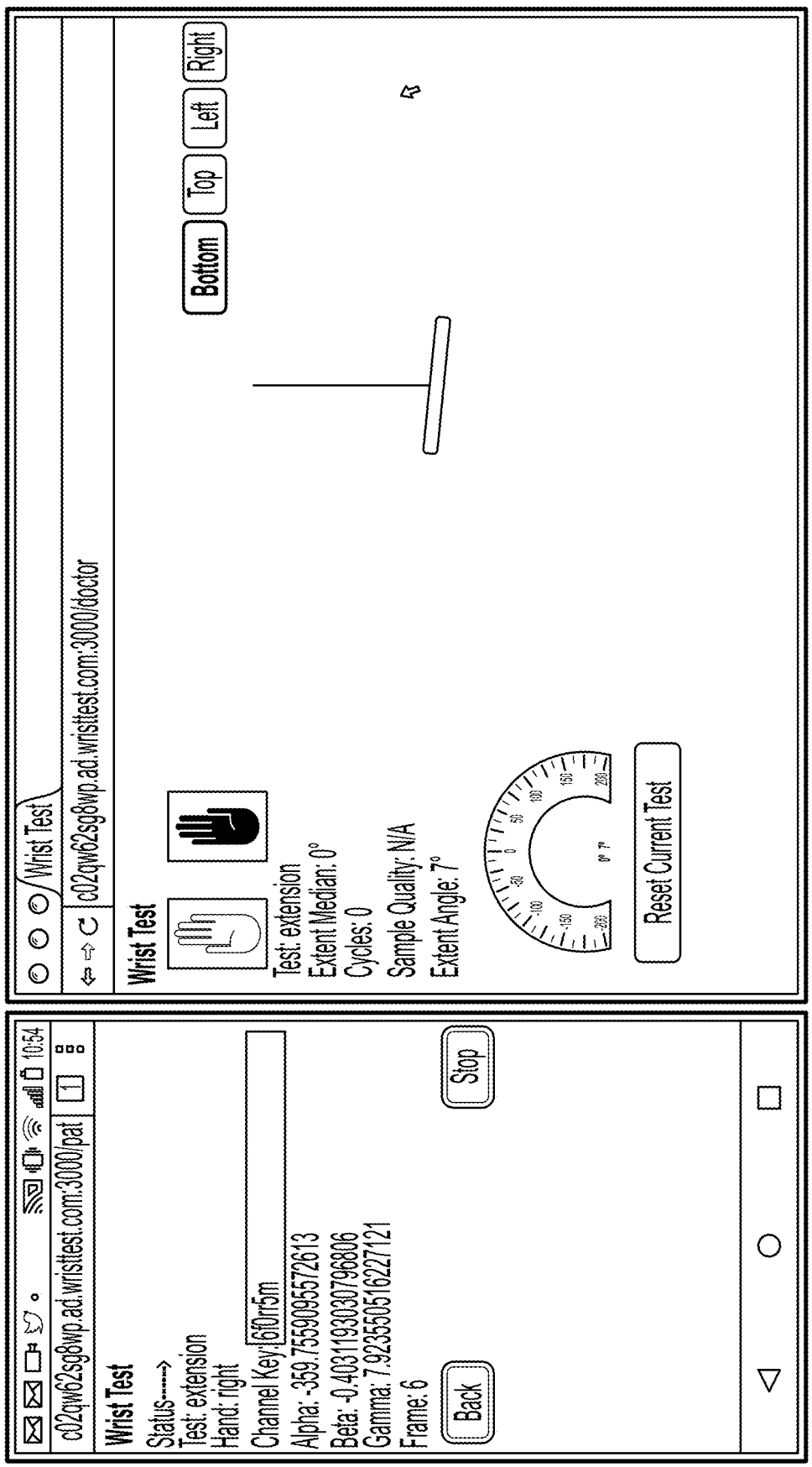
Figure 14:
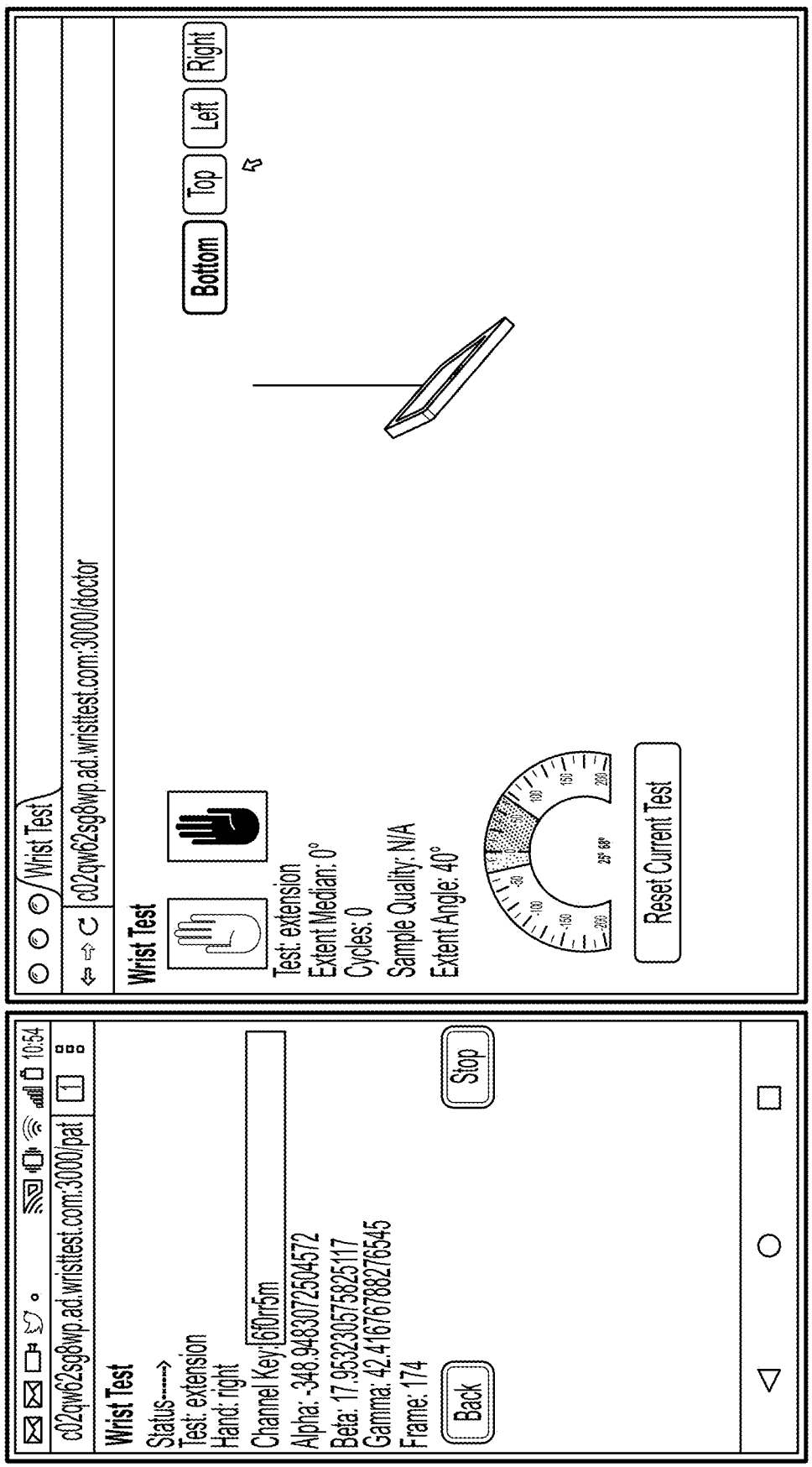
Figure 15:
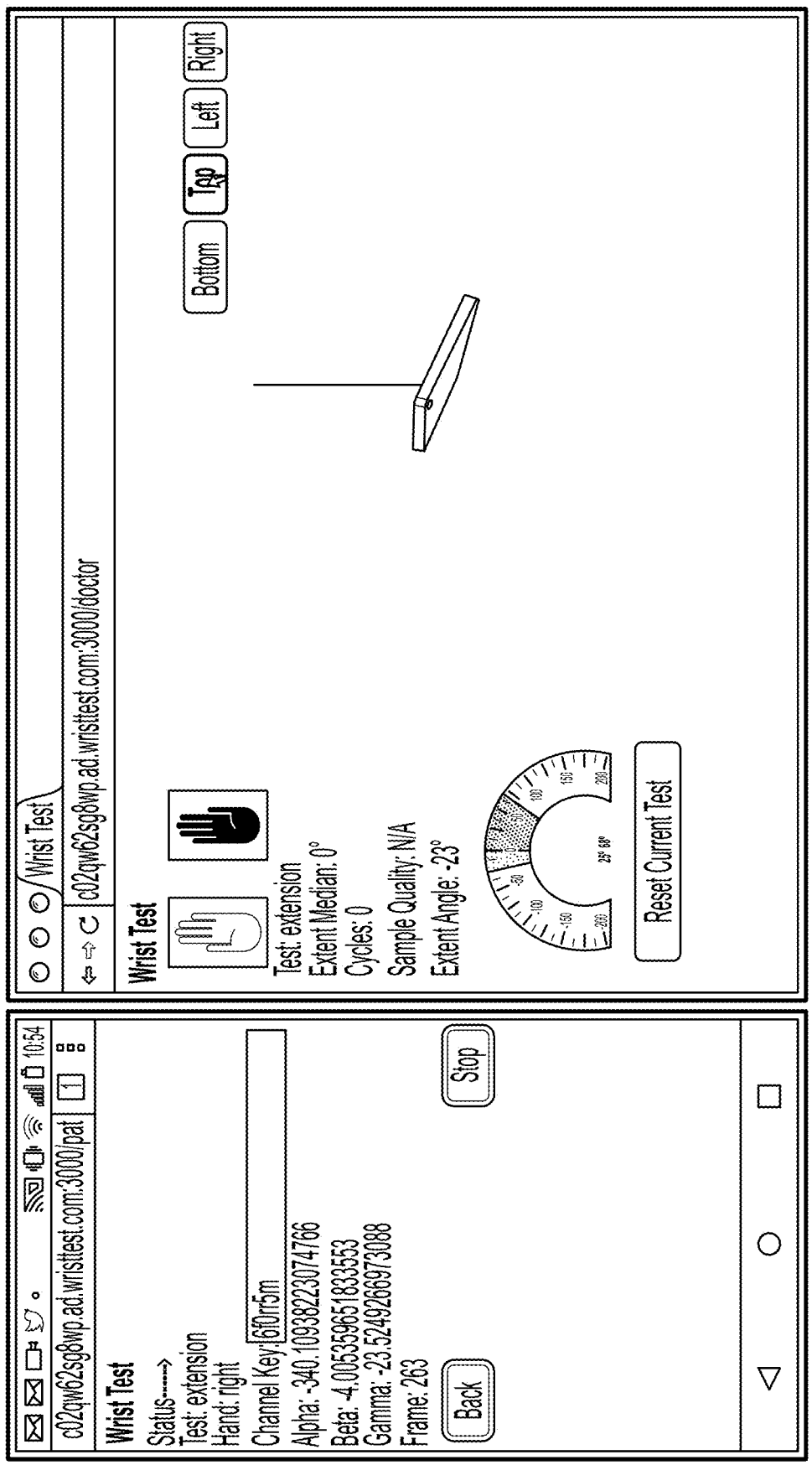
Figure 16:
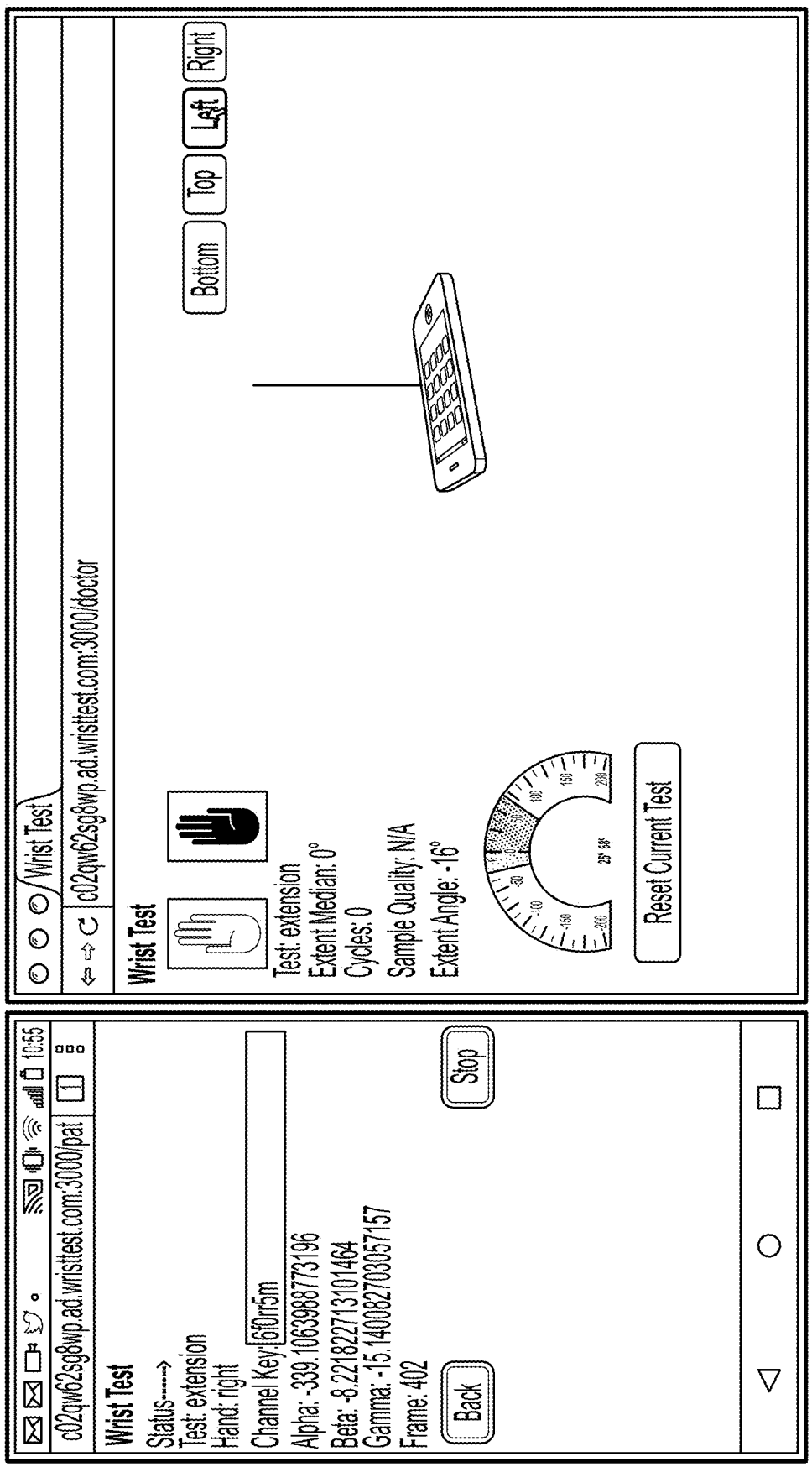
Figure 17:
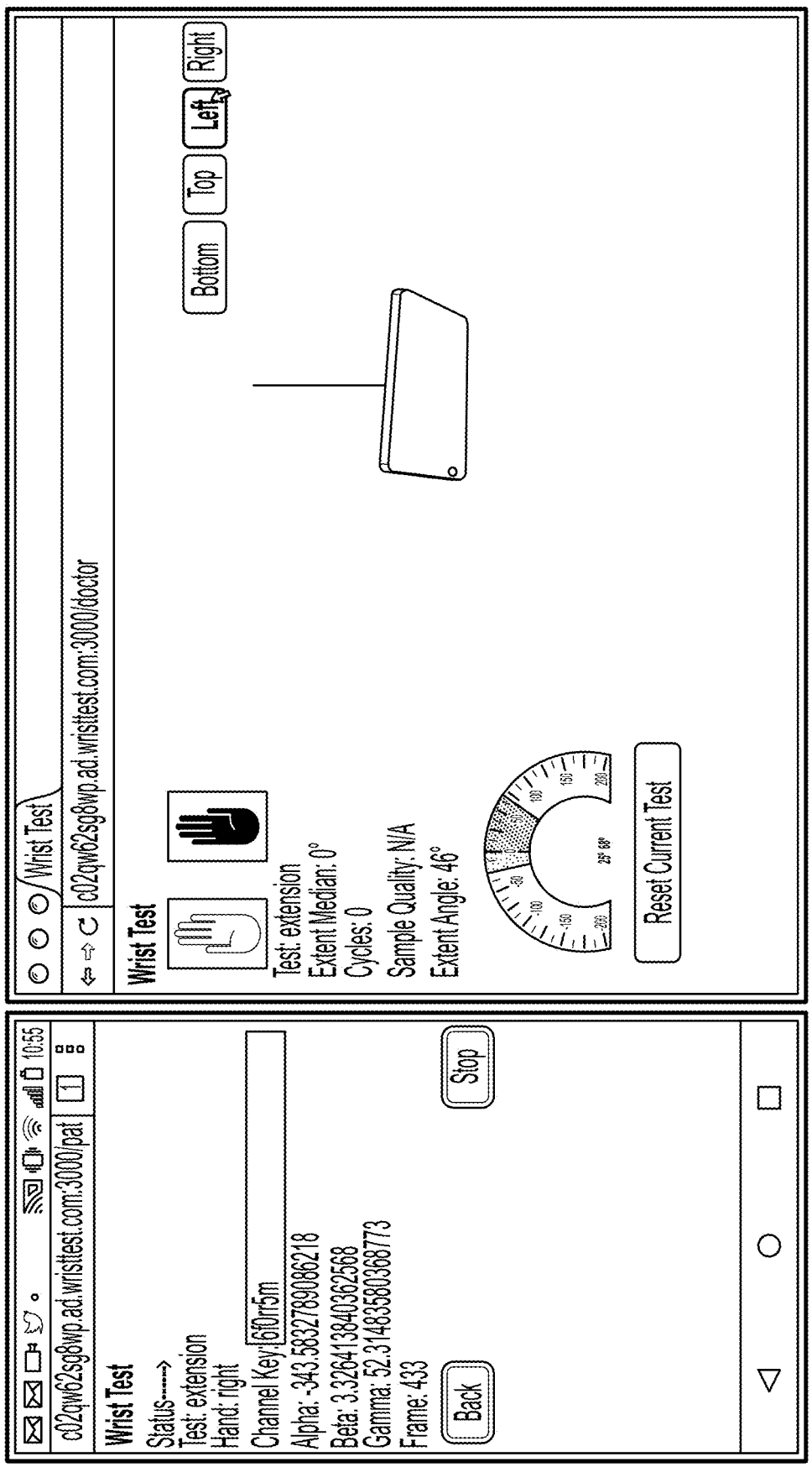
Figure 18:
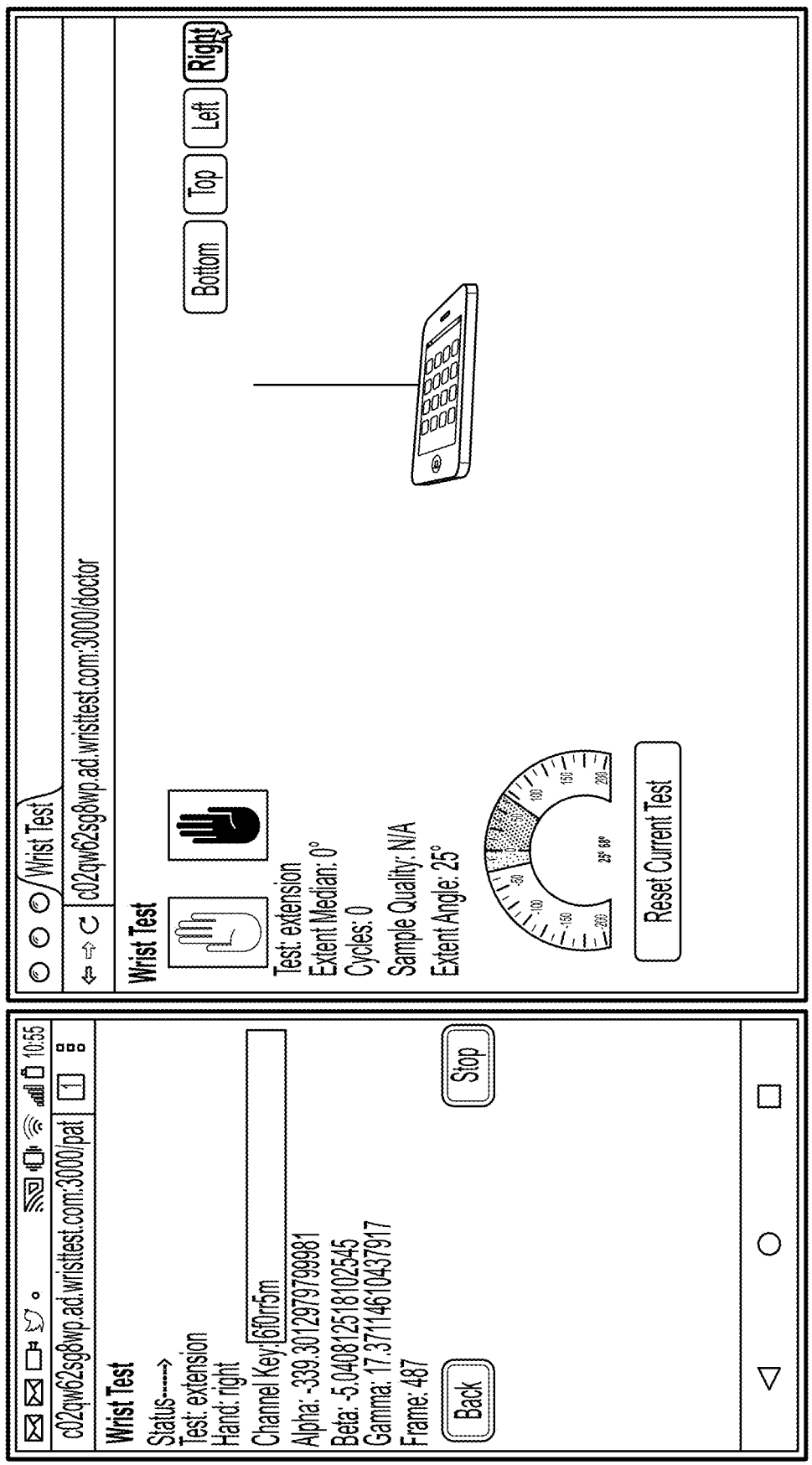

When ready, the subject clicks on the "Next" button, as indicated by the new screen displayed on the subject side of FIG. 12, which shows a status screen for the test. The test is ready to be commenced upon the subject selecting the clickable "Go!" button on the display. FIG. 13 shows the subject and provider sides at the beginning of the actual test. The subject side displays to the subject a continuous indication of performance of the test. The "Alpha," "Beta," and "Gamma" angles vary (Alpha between 0 and ±360°, Beta and Gamma between 0 and ±180°) and the "Frame" value increases as more data are received. In this test, there are approximately 50 frames per second. FIG. 13 also shows that the subject side displays a clickable "Stop" button, allowing the subject to stop the test if desired. The provider side of FIG. 13 shows a three-dimensional representation of the subject's device that provides a substantially real-time and continuous depiction of the subject's device during the test. The provider side also provides graphical and textual indications of the current "Extent Angle." If the Alpha and Beta angles are 0, then the extent angle will equal the Gamma angle. FIG. 14 is a few more seconds into the test and shows on the graphical degree indicator on the provider side that the subject has performed both extension and flexion (showing maximum positive and negative deviations from 0). FIG. 14 also shows that the subject is not keeping the device perfectly within the desired axis, because the provider can see the face of the subject's device. On the subject side, this deviation from desired axis is shown by Alpha and Beta angles diverging from 0. The provider can view the subject's device from four perspectives. The view in the figures up to FIG. 14 has been of the bottom of the device. FIG. 15 shows the provider's view a few seconds later of the top of the subject's device. FIGS. 16 and 17 show the provider's view a few seconds after that of the left side of the subject's device, and FIG. 18 shows the provider's view of the right side of the subject's device.

Figure 19:
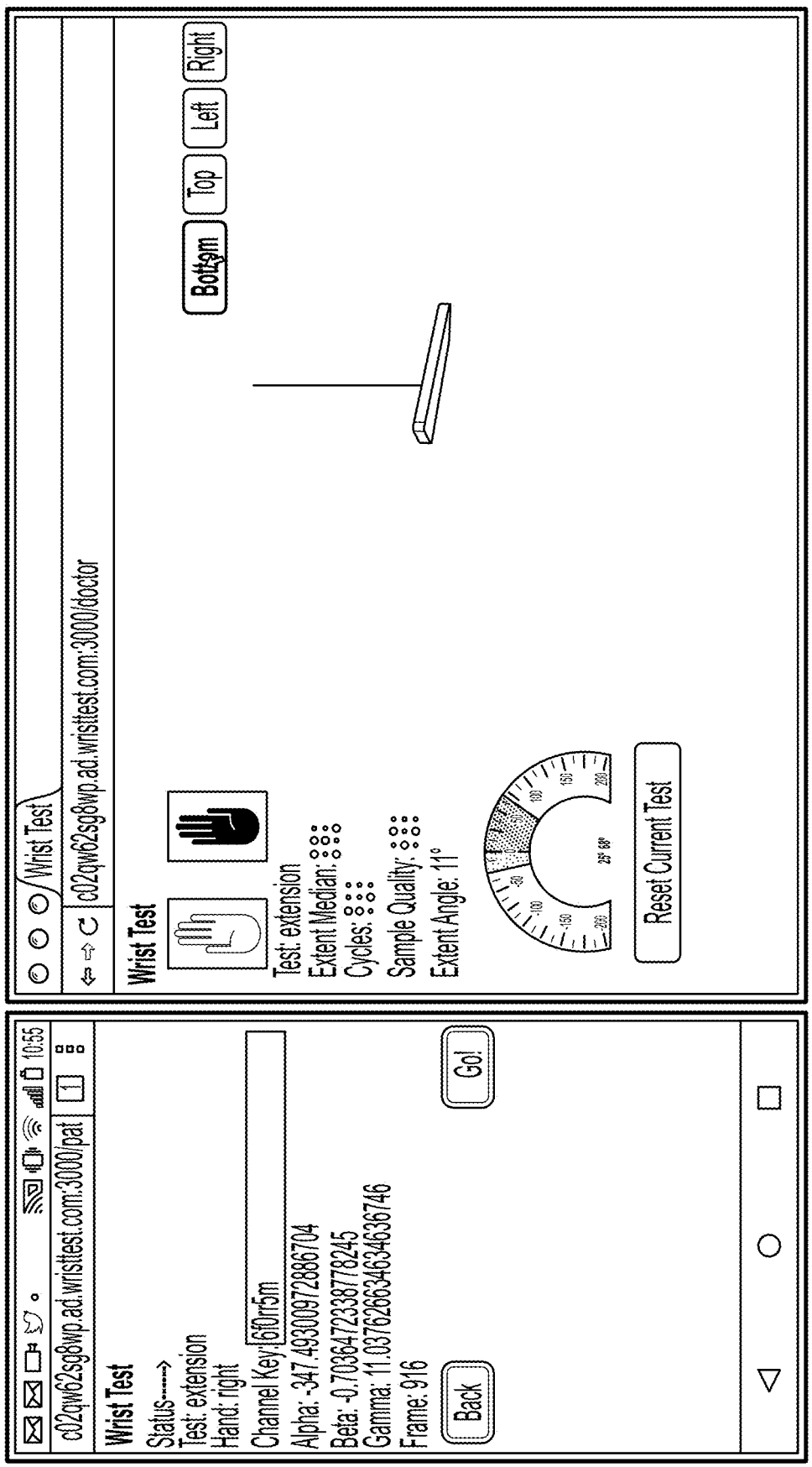
Figure 20:
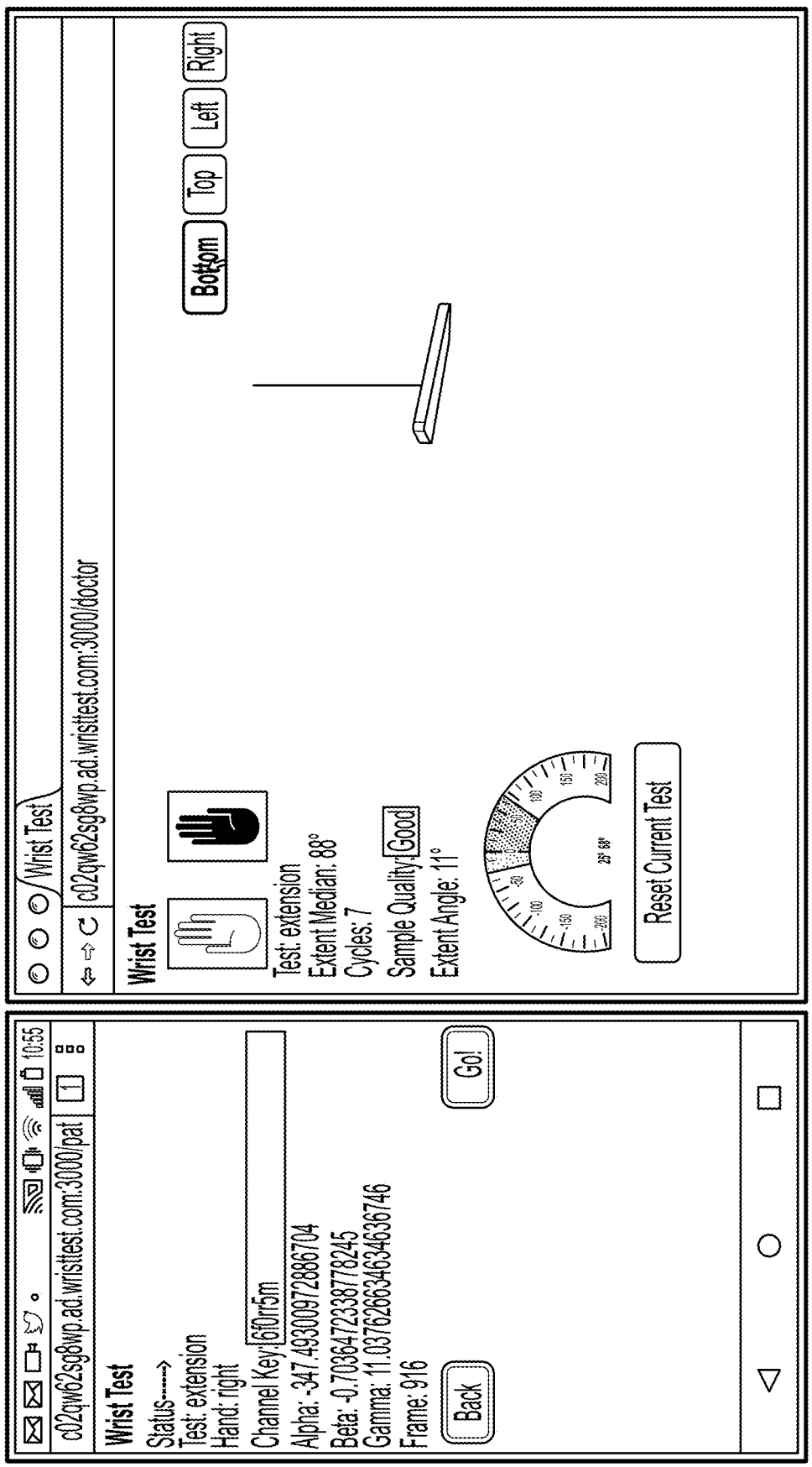
Figure 21:
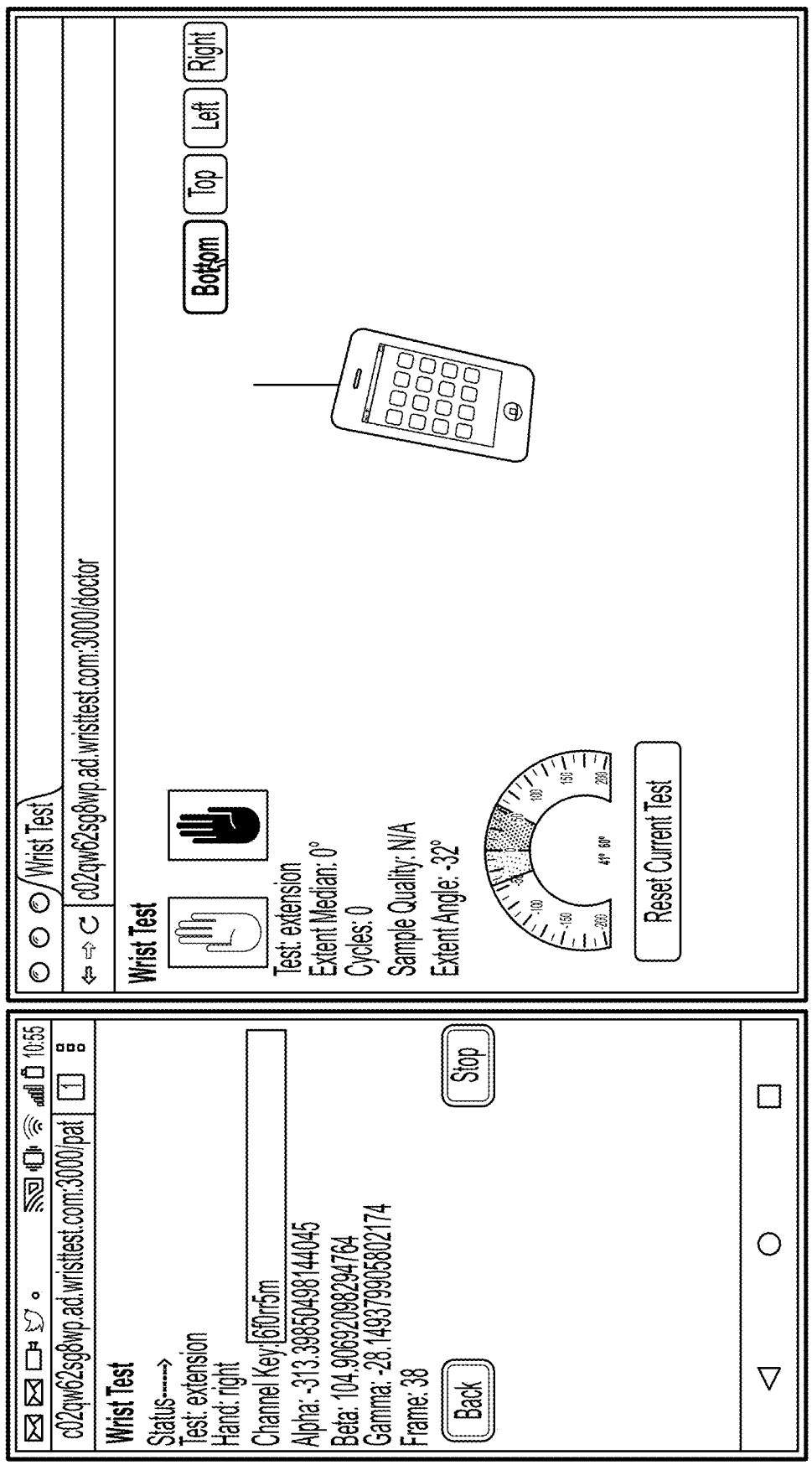
Figure 22:
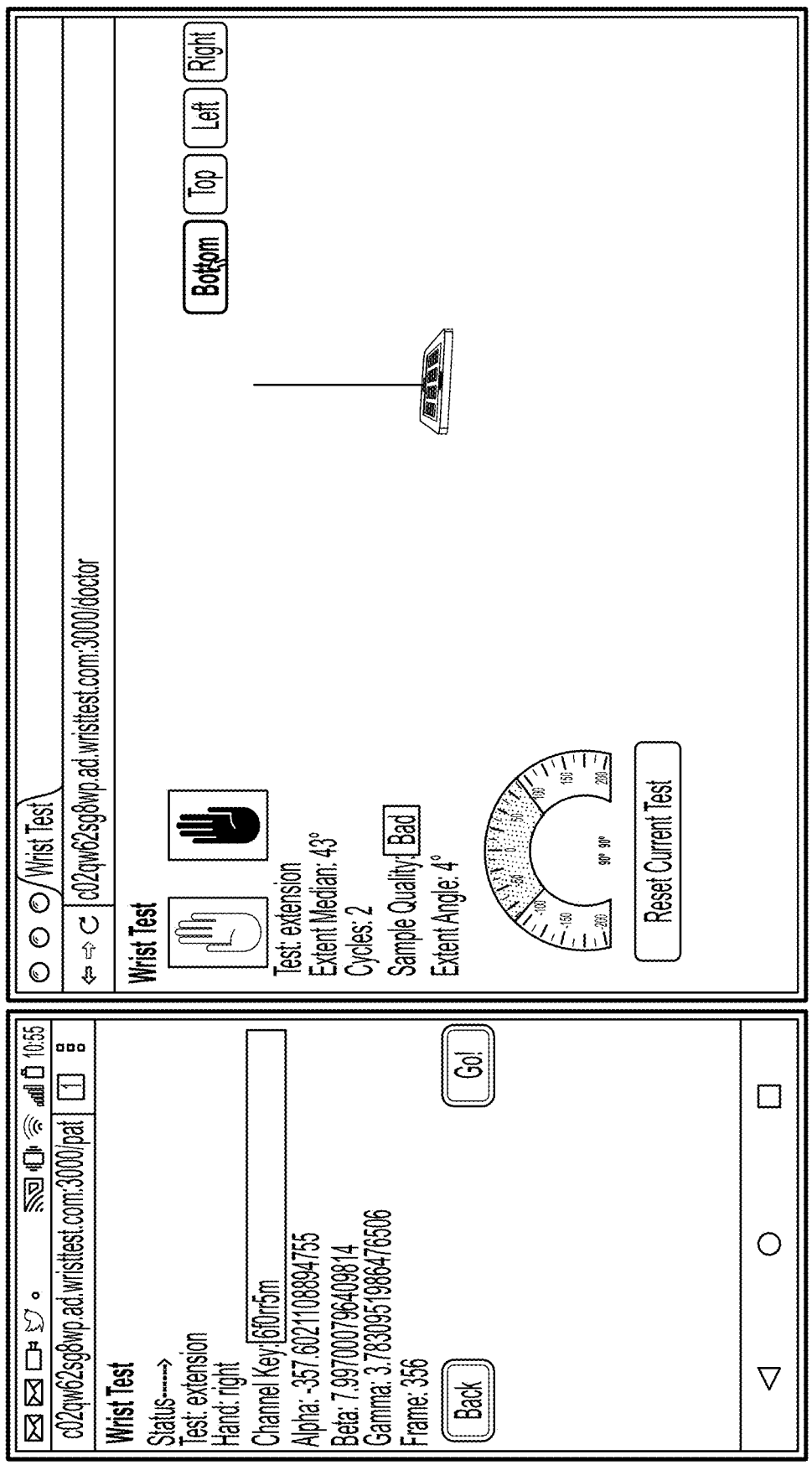

FIG. 19 shows the end of the test: the subject's display stops changing and the "Stop" button becomes a "Go" button, and the values on the provider display for Extent Median, Cycles, and Sample Quality are processing. FIG. 20 shows on the provider that the test was "Good," the Extent Median was 88°, and the number of cycles was 7. FIG. 21 shows the provider clicking on the "Reset Current Test" button to begin a new test. In this test, the subject is purposefully moving the device in axes other than the desired axis—see the large value of Beta and note that the provider can see the full face of the subject device in the "Bottom" view. Unsurprisingly, the test terminates prematurely as shown in FIG. 22 (the number of frames is only 356 compared to 916 in the previous test) and the provider display shows a "Bad" test label.

Accordingly, a remote range-of-motion test is provided that beneficially gives a health care provider real-time feedback of the test's performance and a three-dimensional view of a user's device during the test's performance. Additionally, the user/subject may perform the range-of-motion test remotely without having the burden of having to travel to the health care provider's location.

Aspects of the present invention may be embodied in the form of a system, a computer program product, or a method. Similarly, aspects of the present invention may be embodied as hardware, software or a combination of both. Aspects of the present invention may be embodied as a computer program product saved on one or more computer-readable media in the form of computer-readable program code embodied thereon.

The computer-readable medium may be a computer-readable storage medium or a computer-readable signal medium. A computer-readable storage medium may be, for example, an electronic, optical, magnetic, electromagnetic, infrared, or semiconductor system, apparatus, or device, or any combination thereof.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that may communicate, propagate, or transport a program for use by or in connection with an instruction execution system, apparatus, or device.

Computer program code in embodiments of the present invention may be written in any suitable programming language. The program code may execute on a single computer, or on a plurality of computers. The computer may include a processing unit in communication with a computer-usable medium, where the computer-usable medium contains a set of instructions, and where the processing unit is designed to carry out the set of instructions.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The invention claimed is:

1. An apparatus for performing a remote test of range of motion of a person operating a user device, comprising:
   a transceiver configured to transmit a range-of-motion test link to the user device and to receive motion data from the user device, the user device comprising a sensor that generates the motion data and a second transceiver to communicate with the transceiver;
   a processor configured to calculate in real time, based on the motion data, the continuous position of the user device to enable real-time display to a test provider of the performance of the test and to determine in real time whether the test is performed correctly based on correlating angle measures among multiple frame axes; and
   a display configured to show in real time a continuous indication of the performance of the test and whether the test is performed correctly.

2. The apparatus of claim 1, wherein the indication of the performance of the test comprises motion of the user device.

3. The apparatus of claim 1, wherein the indication of the performance of the test comprises a three-dimensional depiction of the user device.

4. The apparatus of claim 1, wherein the indication of the performance of the test comprises a continuous display of angle of motion.

5. The apparatus of claim 1, wherein the motion data are generated using an accelerometer in the user device.

6. The apparatus of claim 1, wherein the test is an extension-flexion test of the person's wrist.

7. The apparatus of claim 1, wherein the test is a pronation-supination test of the person's wrist.

8. The apparatus of claim 1, wherein the test is a radial-ulnar deviation test of the person's wrist.

9. The apparatus of claim 1, wherein the position of the user device is calculated using a rotation matrix.

10. The apparatus of claim 1, wherein the user device displays real-time data about the test.

11. A method for performing a remote test of range of motion of a person operating a user device, comprising:
    transmitting, with a transceiver, a range-of-motion test link to the user device;
    receiving motion data from the user device, the user device comprising a sensor that generates the motion data and a second transceiver to communicate with the transceiver;
    calculating in real time, based on the motion data, the continuous position of the user device to enable real-time display to a test provider of the performance of the test;

determining in real time whether the test is performed correctly based on correlating angle measures among multiple frame axes; and displaying in real time a continuous indication of the performance of the test and whether the test is performed correctly.

12. The method of claim 11, wherein the indication of the performance of the test comprises motion of the user device.

13. The method of claim 11, wherein the indication of the performance of the test comprises a three-dimensional depiction of the user device.

14. The method of claim 11, wherein the indication of the performance of the test comprises a continuous display of angle of motion.

15. The method of claim 11, wherein the motion data are generated using a gyroscope in the user device.

16. The method of claim 11, wherein the test is an extension-flexion test of the person's wrist.

17. The method of claim 11, wherein the test is a pronation-supination test of the person's wrist.

18. The method of claim 11, wherein the test is a radial-ulnar deviation test of the person's wrist.

19. The method of claim 11, wherein the position of the user device is calculated using a rotation matrix.

20. The method of claim 11, wherein the user device displays real-time data about the test.

* * * * *